United States Patent [19]

Dean et al.

[11] Patent Number: 5,951,964

[45] Date of Patent: *Sep. 14, 1999

[54] TECHNETIUM-99M LABELED PEPTIDES FOR IMAGING

[75] Inventors: Richard T. Dean; John Lister-James, both of Bedford, N.H.

[73] Assignee: Diatide, Inc., Londonderry, N.H.

[ * ] Notice: This patent is subject to a terminal disclaimer.

[21] Appl. No.: 08/341,537

[22] PCT Filed: Jun. 4, 1993

[86] PCT No.: PCT/US93/05372

§ 371 Date: Jan. 26, 1995

§ 102(e) Date: Jan. 26, 1995

[87] PCT Pub. No.: WO93/25244

PCT Pub. Date: Dec. 23, 1993

[51] Int. Cl.$^6$ ............................ A61K 51/08; A61K 38/00
[52] U.S. Cl. ...................... 424/1.69; 530/317; 530/318; 530/300
[58] Field of Search .................. 424/1.41, 1.49, 424/1.69, 9.34, 9.341; 530/300, 318, 317, 391.3; 534/10, 14

[56] References Cited

U.S. PATENT DOCUMENTS

| | | |
|---|---|---|
| 4,434,151 | 2/1984 | Byrne et al. . |
| 4,444,690 | 4/1984 | Fritzberg . |
| 4,571,430 | 2/1986 | Byrne et al. . |
| 4,575,556 | 3/1986 | Byrne et al. . |
| 4,673,562 | 6/1987 | Davison et al. . |
| 4,832,940 | 5/1989 | Ege et al. . |
| 4,861,869 | 8/1989 | Nicolotti et al. . |
| 4,925,648 | 5/1990 | Hanson et al. ........................... 424/1.1 |
| 4,965,392 | 10/1990 | Fritzberg et al. . |
| 5,061,641 | 10/1991 | Shochat et al. . |
| 5,169,933 | 12/1992 | Anderson et al. .................... 530/391.3 |
| 5,196,510 | 3/1993 | Rodwell et al. ......................... 530/324 |
| 5,300,280 | 4/1994 | DeRosch et al. ....................... 424/1.53 |
| 5,326,856 | 7/1994 | Coughlin et al. .......................... 534/14 |
| 5,700,444 | 12/1997 | Zamora et al. ......................... 424/1.69 |

FOREIGN PATENT DOCUMENTS

| | | |
|---|---|---|
| 453082A1 | 8/1991 | European Pat. Off. ....... A61K 39/44 |
| 8901827 | 11/1989 | WIPO . |
| WO 90/03798 | 4/1990 | WIPO . |
| 9001399 | 9/1990 | WIPO . |
| WO9015818 | 12/1990 | WIPO . |
| 91301948 | 10/1991 | WIPO . |
| 9100935 | 12/1991 | WIPO . |
| 9106479 | 4/1992 | WIPO . |

OTHER PUBLICATIONS

Posnett, et al. (1988) "A Novel Method for Producing Anti–peptide Antibodies," The Jrnl of Biological Chemistry, 263, 1719–1725.

*Primary Examiner*—José G. Dees
*Assistant Examiner*—Michael G. Hartley
*Attorney, Agent, or Firm*—Patricia A. McDaniels; Kevin E. Noonan

[57] ABSTRACT

This invention relates to radiolabeled reagents, including specific-binding peptide embodiments thereof, and methods for producing and using such reagents. Specifically, the invention relates to reagents for preparing scintigraphic imaging agents for imaging sites in a mammalian body. Reagents, methods and kits for making such reagents, and methods for using such reagents labeled with technetium-99m (Tc-99m) via Tc-99m binding moieties comprising said reagents, are provided. In particular, the specific-binding peptides and Tc-99m binding moieties comprising the reagents of the invention are covalently linked to a polyvalent linker moiety, so that the polyvalent linker moiety is covalently linked to a multiplicity of the specific-binding peptides, and the Tc-99m binding moieties are covalently linked to a plurality of the specific-binding peptides, the polyvalent linker moiety, or to both the specific-binding peptides and the polyvalent linker moiety.

30 Claims, 1 Drawing Sheet

TECHNETIUM-99M LABELED PEPTIDES FOR IMAGING

BACKGROUND OF THE INVENTION

1. Field of the Invention

This invention relates to radiodiagnostic reagents and peptides, and methods for producing labeled radiodiagnostic agents. Specifically, the invention relates to scintigraphic imaging agents for imaging sites in a mammalian body comprising specific-binding peptides labeled with technetium-99m (Tc-99m) via a radiolabel-binding moiety which forms a complex with Tc-99m. In particular, the peptide reagents of the invention are covalently linked to a polyvalent linker moiety, so that the polyvalent linker moiety is covalently linked to a multiplicity of the specific-binding peptides, and the Tc-99m binding moieties are covalently linked to a plurality of the specific-binding peptides, the polyvalent linker moiety, or to both the specific-binding peptides and the polyvalent linker moiety. Methods and kits for making such reagents, and methods for using such reagents are also provided.

2. Description of the Prior Art

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. Tc-99m is a preferred radionuclide because it emits gamma radiation at 140 keV, it has a physical half-life of 6 hours, and it is readily available on-site using a molybdenum-99/technetium-99m generator.

The sensitivity of imaging methods using radioactively-labeled peptides is much higher than other radiopharmaceuticals known in the art, since the specific binding characteristic of a specific binding peptide moiety concentrates the radioactive signal over the area of interest. Small synthetic peptides that bind specifically to targets of interest may be advantageously used as the basis for radiotracers. This is because: 1. they may be synthesized chemically (as opposed to requiring their production in a biological system such as bacteria or mammalian cells, or their isolation from a biologically-derived substance such as a fragment of a protein); 2. they are small, so that non-target bound radiotracer is rapidly eliminated from the body, thereby reducing background (non-target) radioactivity and allowing good definition of the target; and 3. small peptides may be readily manipulated chemically to optimize their affinity for a particular binding site.

Small readily synthesized labeled peptide molecules are preferred as routinely-used radiopharmaceuticals. There is clearly a need for small synthetic labeled peptides that can be directly injected into a patient and will image pathological sites by localizing at such sites. Tc-99m labeled small synthetic peptides offer clear advantages as radiotracers for gamma scintigraphy, due to the properties of Tc-99m as a radionuclide for imaging and the utility of specific-binding small synthetic peptides as radiotracer molecules.

Radiolabeled proteins and peptides have been reported in the prior art.

Ege et al., U.S. Pat. No. 4,832,940 teach radiolabeled peptides for imaging localized T-lymphocytes.

Olexa et al., 1982, European Patent Application No. 823017009 disclose a pharmaceutically acceptable radiolabeled peptide selected from Fragment $E_1$ isolated from cross-linked fibrin, Fragment $E_2$ isolated from cross-linked fibrin, and peptides having an amino acid sequence intermediate between Fragments $E_1$ and $E_2$.

Ranby et al., 1988, PCT/US88/02276 disclose a method for detecting fibrin deposits in an animal comprising covalently binding a radiolabeled compound to fibrin.

Hadley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Lees et al., 1989, PCT/US89/01854 teach radiolabeled peptides for arterial imaging.

Sobel, 1989, PCT/US89/02656 discloses a method to locate the position of one or more thrombi in an animal using radiolabeled, enzymatically inactive tissue plasminogen activator.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Maraganore et al., 1991, PCT/US90/04642 disclose a radiolabeled thrombus inhibitor comprising (a) a inhibitor moiety; (b) a linker moiety; and (c) and anion binding site moiety.

Rodwell et al., 1991, PCT/US91/03116 disclose conjugates of "molecular recognition units" with "effector domains".

Tubis et al., 1968, Int. J. Appl. Rad. Isot. 19: 835–840 describe labeling a peptide with technetium-99m.

Sundrehagen, 1983, Int. J. Appl. Rad. Isot. 34: 1003 describes labeling polypeptides with technetium-99m.

Although optimal for radioimaging, the chemistry of Tc-99m has not been as thoroughly studied as the chemistry of other elements and for this reason methods of radiolabeling with technetium-99m are not abundant. Tc-99m is normally obtained as Tc-99m pertechnetate ($TcO_4^-$; technetium in the +7 oxidation state), usually from a molybdenum-99/technetium-99m generator. However, pertechnetate does not bind well to other compounds. Therefore, in order to radiolabel a peptide, Tc-99m pertechnetate must be converted to another form. Since technetium does not form a stable ion in aqueous solution, it must be held in such solutions in the form of a coordination complex that has sufficient kinetic and thermodynamic stability to prevent decomposition and resulting conversion of Tc-99m either to insoluble technetium dioxide or back to pertechnetate.

For the purpose of radiolabeling, it is particularly advantageous for the Tc-99m complex to be formed as a chelate in which all of the donor groups surrounding the technetium ion are provided by a single chelating ligand. This allows the chelated Tc-99m to be covalently bound to a peptide through a single linker between the chelator and the peptide.

These ligands are sometimes referred to as bifunctional chelating agents having a chelating portion and a linking portion. Such compounds are known in the prior art.

Byrne et al., U.S. Pat. No. 4,434,151 describe homocysteine thiolactone-derived bifunctional chelating agents that can couple radionuclides to terminal amino-containing compounds that are capable of localizing in an organ or tissue to be imaged.

Fritzberg, U.S. Pat. No. 4,444,690 describes a series of technetium-chelating agents based on 2,3-bis (mercaptoacetamido) propanoate.

Byrne et al., U.S. Pat. No. 4,571,430 describe novel homocysteine thiolactone bifunctional chelating agents for chelating radionuclides that can couple radionuclides to terminal amino-containing compounds that are capable of localizing in an organ or tissue to be imaged.

Byrne et al., U.S. Pat. No. 4,575,556 describe novel homocysteine thiolactone bifunctional chelating agents for chelating radionuclides that can couple radionuclides to terminal amino-containing compounds that are capable of localizing in an organ or tissue to be imaged.

Davison et al., U.S. Patent No. 4,673,562 describe technetium chelating complexes of bisamido-bisthio-ligands and salts thereof, used primarily as renal function monitoring agents.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Fritzberg et al., European Patent Application No. 86100360.6 describe dithiol, diamino, or diamidocarboxylic acid or amine complexes useful for making technetium-labeled imaging agents.

Dean et al., 1989, PCT/US89/02634 describe bifunctional coupling agents for radiolabeling proteins and peptides.

Flanagan et al., European Patent Application No. 90306428.5 disclose Tc-99m labeling of synthetic peptide fragments via a set of organic chelating molecules.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Dean, co-pending U.S. patent application Ser. No. 07/653, 012 teaches reagents and methods for preparing peptides comprising a Tc-99m chelating group covalently linked to a specific binding peptide for radioimaging in vivo, and is hereby incorporated by reference.

Baidoo & Lever, 1990, Bioconjugate Chem. 1: 132–137 describe a method for labeling biomolecules using a bisamine bisthiol group that gives a cationic technetium complex.

It is possible to radiolabel a peptide by simply adding a thiol-containing moiety such as cysteine or mercaptoacetic acid. Such procedures have been described in the prior art.

Schochat et al., U.S. Pat. No. 5,061,641 disclose direct radiolabeling of proteins comprised of at least one "pendent" sulfhydryl group.

Dean et al., co-pending U.S. patent application Ser. No. 07/807,062 teach radiolabeling peptides via attached groups containing free thiols, and is incorporated herein by reference.

Goedemans et al., PCT Application No. WO 89/07456 describe radiolabeling proteins using cyclic thiol compounds, particularly 2-iminothiolane and derivatives.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes Tc-99m labeling of RGD-containing oligopeptides.

Although it is possible to label specific binding peptides with Tc-99m (as disclosed in co-pending U.S. patent application Ser. No. 07/653,012, now abandoned, a divisional of which issued as U.S. Pat. No. 5,654,272; Ser. No. 07/807, 062, now U.S. Pat. No. 5,443,815; Ser. No. 07/871,282, a divisional of which issued as U.S. Pat. No. 5,780,007; Ser. No. 07/886,752, now abandoned, a divisional of which issued as U.S. Pat. No. 5,736,122; Ser. No. 07/893,981, now U.S. Pat. No. 5,508,020; Ser. Nos. 07/955,466; 08/019,864, now U.S. Pat. No. 5,552,525; and Ser. No. 08/044,825, now abandoned, which issued as U.S. Pat. No. 5,645,815, and PCT International Applications PCT/US92/00757, PCT/US92/10716, PCT/US93/02320 and PCT/US93/04794, hereby incorporated by reference), some such peptides exhibit low binding site affinity whereby the strength of peptide binding to the target site is insufficient to allow enough of the radioisotope to localize at the targeted site to form a radioimage. In an effort to solve this problem, peptides comprised of linear arrays of specific binding peptide repeating units have been described in the prior art.

Rodwell et al., 1991, PCT/US91/03116 disclose linear arrays of the peptide sequence RGD.

However, alternative arrangements of specific binding peptide units may be preferable.

SUMMARY OF THE INVENTION

The present invention provides reagents useful in preparing radioimaging agents. The present invention provides reagents comprised of a multiplicity of specific-binding peptide moieties, having an affinity for targeted sites in vivo sufficient to produce a scintigraphically-detectable image. The incorporation of a multiplicity of specific-binding peptide moieties in the reagents of the invention permits the use of specific binding peptides whose individual binding affinity would not otherwise be sufficient to produce a scintigraphically-detectable image in vivo. In other cases, an improvement in otherwise acceptable scintigraphic images produced by a particular specific-binding peptide is achieved using the reagents of this invention.

The present invention provides reagents for preparing scintigraphic imaging agents comprising a multiplicity of specific-binding peptide moieties covalently linked to a polyvalent linker moiety, wherein technetium-99m binding moieties are covalently linked to the specific-binding peptides, the polyvalent linker moiety, or to both the specific-binding peptides and the polyvalent linker moieties.

The invention also provides Tc-99m labeled scintigraphic imaging agents prepared from such peptide reagents. The specific-binding peptides of the invention are comprised of peptides that specifically bind to a target in vivo.

In a first aspect of the present invention, the invention provides reagents capable of being Tc-99m labeled for imaging sites within a mammalian body, comprising a multiplicity of specific binding peptides each having an amino acid sequence of 3–100 amino acids, covalently linked to a polyvalent linking moiety, and further comprising Tc-99m binding moieties covalently linked to a plurality of the specific-binding peptides, the polyvalent linker moiety, or both. Preferred embodiments of the invention comprise linear and cyclic specific binding peptides.

In a second aspect, the present invention provides reagents capable of being Tc-99m labeled for imaging sites within a mammalian body, comprising a multiplicity of specific binding peptides having an amino acid sequence of 3–100 amino acids, covalently linked to a polyvalent linking moiety, and a further comprising Tc-99m binding moiety covalently linked to a plurality of the specific-binding peptides, the polyvalent linker moiety, or both, wherein the Tc-99m binding moiety has formula:

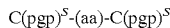

wherein $C(pgp)^S$ is a protected cysteine and (aa) is an amino acid. In a preferred embodiment, the amino acid is glycine. In a preferred embodiment, the peptide comprises between 3 and 30 amino acids. Preferred embodiments of the invention comprise linear and cyclic specific binding peptides.

In a third embodiment, the invention provides reagents capable of being Tc-99m labeled for imaging sites within a mammalian body, comprising a multiplicity of specific binding peptides having an amino acid sequence of 3–100 amino acids, covalently linked to a polyvalent linking moiety, and further comprising a Tc-99m binding moiety covalently linked to a plurality of the specific-binding peptides, the polyvalent linker moiety, or both, wherein the Tc-99m binding moiety comprises a single thiol having a formula:

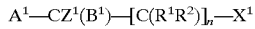

wherein
- $A^1$ is H, HOOC, $H_2$NOC, or —NHOC;
- $B^1$ is SH or $NHR^3$;
- $X^1$ is H, methyl, SH or $NHR^3$;
- $Z^1$ is H or methyl;
- $R^1$ and $R^2$ are independently H or lower alkyl;
- $R^3$ is H, lower alkyl or —C=O;
- n is 0, 1 or 2;

and where $B^1$ is $NHR^3$, $X^1$ is SH, $Z^1$ is H and n is 1 or 2; where $X^1$ is $NHR^3$, $B^1$ is SH, $Z^1$ is H and n is 1 or 2; where $B^1$ is H, $A^1$ is HOOC, $H_2$NOC, or NHOC, $X^1$ is SH, $Z^1$ is H and n is 0 or 1; where $Z^1$ is methyl, $X^1$ is methyl, $A^1$ is HOOC, $H_2$NOC, or —NHOC, $B^1$ is SH and n is 0; and wherein the thiol moiety is in the reduced form. In a preferred embodiment, the peptide is comprised between 3 and 30 amino acids. Preferred embodiments of the invention comprise linear and cyclic specific binding peptides.

In another embodiment, the invention provides peptide reagents capable of being Tc-99m labeled for imaging sites within a mammalian body comprising a multiplicity of specific binding peptides having an amino acid sequence of 3–100 amino acids, covalently linked to a polyvalent linking moiety, and further comprising a Tc-99m binding moiety covalently linked to a plurality of the specific-binding peptides, the polyvalent linker moiety, or both, wherein the Tc-99m binding moiety has formula:

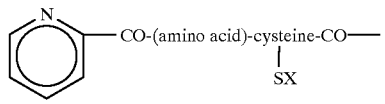

[for purposes of this invention, radiolabel-binding moieties having this structure will be referred to as picolinic acid (Pic)-based moieties] or

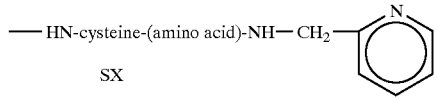

wherein X is H or a protecting group and (amino acid) is any amino acid. For purposes of this invention, radiolabel-binding moieties having this structure will be referred to as picolylamine (Pica)-based moieties. In a preferred embodiment, the amino acid is glycine and X is an acetamidomethyl protecting group. In additional preferred embodiments, the peptide is comprised between 3 and 30 amino acids. Preferred embodiments of the invention comprise linear and cyclic specific binding peptides.

Yet another embodiment of the invention provides peptide reagents capable of being labeled with Tc-99m for imaging sites within a mammalian body, comprising a multiplicity of specific binding peptides having an amino acid sequence of 3–100 amino acids, covalently linked to a polyvalent linking moiety, and further comprising a Tc-99m binding moiety covalently linked to the specific-binding peptides, the polyvalent linker moiety, or both, wherein the Tc-99m binding moiety has formula:

I.

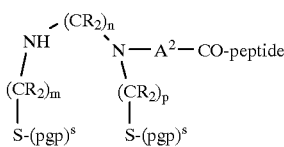

wherein each R can be independently H, $CH_3$ or $C_2H_5$; each $(pgp)^S$ can be independently a thiol protecting group or H; m, n and p are independently 2 or 3; $A^2$ is linear or cyclic lower alkyl, aryl, heterocyclyl, combinations or substituted derivatives thereof; and X is peptide; and

II.

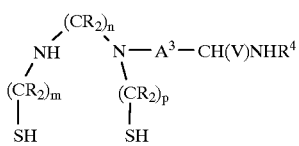

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; $R^4$ is H or peptide; provided that when V is H, $R^4$ is peptide and when $R^4$ is H, V is peptide. [For purposes of this invention, radiolabel-binding moieties having these structures will be referred to as "BAT" moieties]. Preferred embodiments of the invention comprise linear and cyclic specific binding peptides.

The reagents of the invention are provided wherein the specific binding peptides or the radiolabel-binding moieties or both are covalently linked to a polyvalent linking moiety. Polyvalent linking moieties of the invention are comprised of at least 2 identical linker functional groups capable of covalently bonding to specific binding peptides or Tc-99m binding moieties. Preferred linker functional groups are primary or secondary amines, hydroxyl groups, carboxylic acid groups or thiol-reactive groups. In preferred embodiments, the polyvalent linking moieties are comprised of a multiplicity of polyvalent linking moieties covalently linked to form a branched polyvalent linking moiety. In preferred embodiments, the polyvalent linking moieties are comprised of lysine, bis-succinimdylmethylether (BSME), 4-(2,2-dimethylacetyl)benzoic acid (DMAB), tris(succinimidylethyl)amine (TSEA), N-[2-(N',N'-bis(2-succinimidoethyl) aminoethyl)]-$N^6,N^9$-bis(2-methyl-2-mercaptopropyl)-6,9-diazanonanamide (BAT-BS), 4-(O-$CH_2$CO-Gly-Gly-Cys.amide)acetophenone (ETAC) and bis-succinimidohexane (BSH).

The invention also comprises scintigraphic imaging agents that are complexes of the reagents of the invention with Tc-99m and methods for radiolabeling the reagents of the invention with Tc-99m. Radiolabeled complexes provided by the invention are formed by reacting the reagents of the invention with Tc-99m in the presence of a reducing agent. Preferred reducing agents include but are not limited to dithionite ion, stannous ion, and ferrous ion. Complexes of the invention are also formed by labeling the reagents of the invention with Tc-99m by ligand exchange of a prereduced Tc-99m complex as provided herein.

The invention also provides kits for preparing scintigraphic imaging agents that are the reagents of the invention radiolabeled with Tc-99m. Kits for labeling the reagents of the invention with Tc-99m are comprised of a sealed vial containing a predetermined quantity of a reagent of the invention or mixtures thereof and a sufficient amount of reducing agent to label the reagent with Tc-99m.

This invention provides methods for preparing reagents of the invention by chemical synthesis in vitro. In preferred embodiments, peptides are synthesized by solid phase peptide synthesis.

This invention provides methods for using scintigraphic imaging agents that are Tc-99m labeled reagents for imaging a site within a mammalian body by obtaining in vivo gamma scintigraphic images. These methods comprise administering an effective diagnostic amount of a Tc-99m radiolabeled reagent of the invention and detecting the gamma radiation emitted by the Tc-99m localized at the site within the mammalian body.

Specific preferred embodiments of the present invention will become evident from the following more detailed description of certain preferred embodiments and the claims.

DETAILED DESCRIPTION OF THE INVENTION

Figure 1:
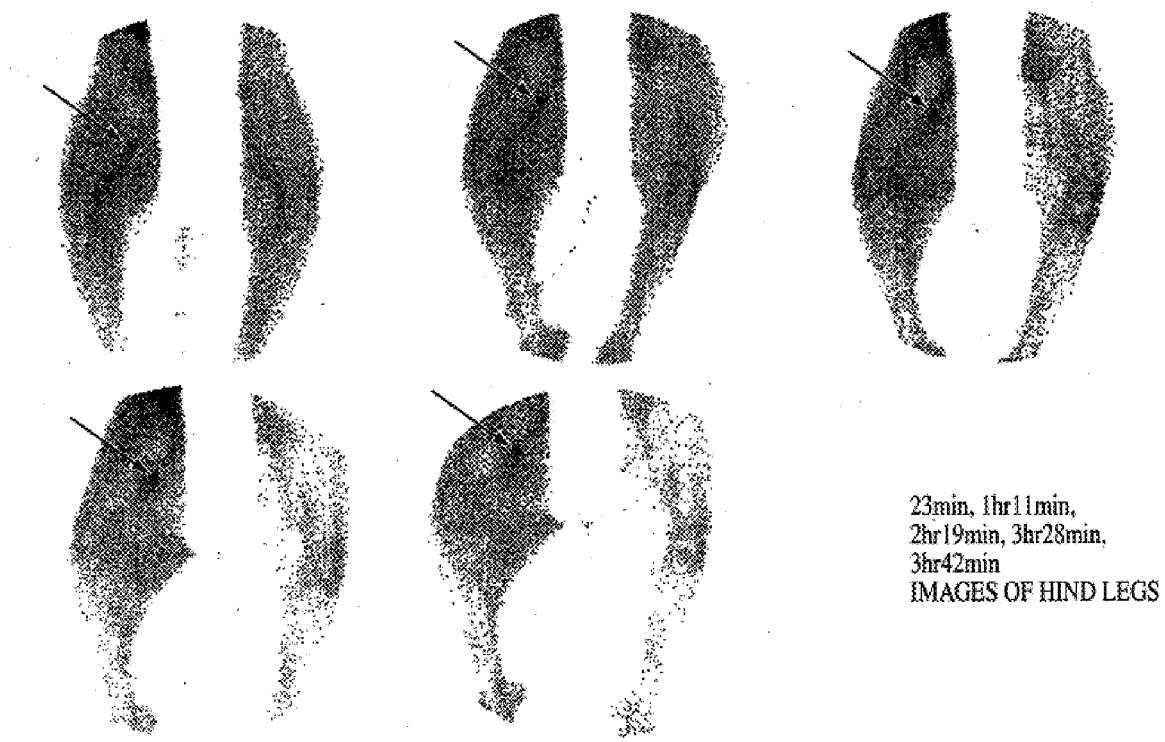
FIG. 1 illustrates a gamma-scintiphoto of deep-vein thrombus imaging in mongrel dogs using Tc-99m labeled scintigraphic imaging agents of the invention as described in Example 5.

The present invention provides reagents, including peptide reagents, for preparing Tc-99m labeled scintigraphic imaging agents for imaging target sites within a mammalian body comprising a multiplicity of specific binding peptides having an amino acid sequence of 3–100 amino acids, covalently linked to a polyvalent linking moiety, and further comprising a Tc-99m binding moiety covalently linked to the specific-binding peptides, the polyvalent linker moiety, or both.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

In the radiolabel binding moieties and peptides covalently linked to such moieties that contain a thiol covalently linked to a thiol protecting groups [(pgp)$^S$] provided by the invention, the thiol-protecting groups may be the same or different and may be but are not limited to:

- —$CH_2$-aryl (aryl is phenyl or alkyl or alkyloxy substituted phenyl);
- —CH-(aryl)$_2$, (aryl is phenyl or alkyl or alkyloxy substituted phenyl);
- —C-(aryl)$_3$, (aryl is phenyl or alkyl or alkyloxy substituted phenyl);
- —$CH_2$-(4-methoxyphenyl);
- —CH-(4-pyridyl)(phenyl)$_2$;
- —C($CH_3$)$_3$;
- —9-phenylfluorenyl;
- —$CH_2$NHCOR (R is unsubstituted or substituted alkyl or aryl);
- —$CH_2$—NHCOOR (R is unsubstituted or substituted alkyl or aryl);
- —CONHR (R is unsubstituted or substituted alkyl or aryl);
- —$CH_2$—S—$CH_2$-phenyl Preferred protecting groups have the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D-amino acids, naturally occurring and otherwise. Reagents comprising specific-binding peptides provided by the invention include but are not limited to the following (the amino acids in the following peptides are L-amino acids except where otherwise indicated):

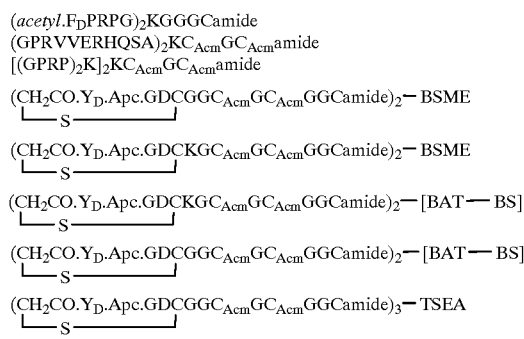

-continued (CH₂CO.Y_D.Apc.GDCGGC_AcmGC_AcmGGCamide)₂— BSH
└── S ──┘
(acetyl.CC_AcmGC_AcmPLYKKIIKKLLES)₂— BSME
(acetyl.CC_AcmGC_AcmGGPLYKKIIKKLLES)₂— BSME
(formyl.MLFK(N_ε — BAT)GGC_AcmGC_AcmGGC.amide)₂— BSME
(CC_AcmGC_AcmGGRGDS)₃— TSEA
(GPRPC_AcmGC_AcmCamide)₃— TSEA
(GPRPPPGGC_AcmGC_AcmGGCamide)₃— TSEA
(Pic.SC_AcmSYNRGDSTCamide)₃— TSEA
(RALVDTLKGGC_AcmGC_AcmCamide)₃— TSEA
(ma.GGGRALVDTLKFVTQAEGAKamide)₂— [BAT— BS]
(GRGDFC_AcmGC_AcmCamide)₃— TSEA
(Pic.GC_AcmRALVDTLKFVTQAEGAKCamide)₃— TSEA
(acetyl.SYNRGDTC_AcmGC_AcmCamide)₃— DMAB (Single-letter abbreviations for amino acids can be found in G. Zubay, *Biochemistry* (2d. ed.), 1988 (MacMillen Publishing: New York) p.33; other abbreviations are as in the Legend to Table I). This list of reagents provided by the invention is illustrative and not intended to be limiting or exclusive, and it will be understood by those with skill in the art that reagents comprising combinations of the peptides disclosed herein or their equivalents may be covalently linked to any of the chelating moieties of the invention and be within its scope, including combinations of such peptides and chelating moieties comprising linking groups as disclosed herein.

Polyvalent linking moieties are covalently linked to the specific peptides of the invention, the Tc-99m binding moieties, or both. Polyvalent linking moieties provided by the invention are comprised of at least 2 linker functional groups capable of covalently bonding to specific binding peptides or Tc-99m binding moieties. Such functional groups include but are not limited to primary and secondary amines, hydroxyl groups, carboxylic acid groups and thiol reactive groups. Polyvalent linking moieties are comprised of preferably at least three functional groups capable of being covalently linked to specific binding peptides or technetium-99m binding moieties. Preferred polyvalent linking moieties include amino acids such as lysine, homolysine, ornithine, aspartic acid and glutamic acid; linear and cyclic amines and polyamines; polycarboxylic acids; and activated thiols such as di- and tri-maleimides. Also preferred are embodiments wherein the polyvalent linking moieties comprise a multiplicity of polyvalent linking moieties covalently linked to form a branched polyvalent linking moiety. For the purposes of this invention, the term "branched" polyvalent linking moieties is intended to include but are not limited to polyvalent linking moieties having formula:

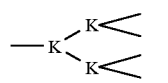

I

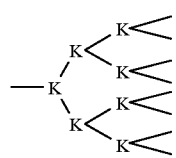

II

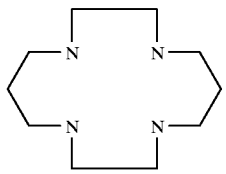

III

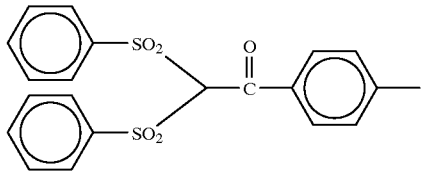

IV

Specific-binding peptides of the present invention can be chemically synthesized in vitro. Such peptides can generally advantageously be prepared on an amino acid synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments [e.g., Pic-Gly-Cys(protecting group)-] comprising picolinic acid (Pic-), the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys-chelator are provided in the Examples hereinbelow. This invention provides for the incorporation of these chelators into virtually any peptide, resulting in a radiolabeled peptide having Tc-99m held as neutral complex.

This invention also provides specific-binding small synthetic peptides which incorporate bisamine bisthiol (BAT) chelators which may be labeled with Tc-99m, resulting in a radiolabeled peptide having Tc-99m held as neutral complex.

In forming a complex of radioactive technetium with the reagents of this invention, the technetium complex, preferably a salt of Tc-99m pertechnetate, is reacted with the reagents of this invention in the presence of a reducing agent. Preferred reducing agents are dithionite, stannous and ferrous ions; the most preferred reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-99m labeled reagents is provided. An appropriate amount of a reagent is introduced into a vial containing a reducing agent, such as stannous chloride or a solid-phase reducing agent, in an amount sufficient to label the reagent with Tc-99m. An appropriate amount of a transfer ligand as described (such as tartrate, citrate, gluconate or mannitol, for example) can also be included. Technetium-99m labeled scintigraphic imaging agents according to the present invention can be prepared by the addition of an appropriate amount of Tc-99m or Tc-99m complex into the vials and reaction under conditions described in Example 4 hereinbelow. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form. Radiolabeled scintigraphic imaging reagents according to the present invention may be prepared by reaction under conditions described in Example 3 hereinbelow.

Radioactively labeled reagents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Technetium-99m labeled scintigrapgic imaging agents provided by the present invention can be used for visualizing sites in a mammalian body. In accordance with this invention, the technetium-99m labeled scintigraphic imaging agents are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the organ or tumor in vivo can take place in a matter of a few minutes. However, imaging can take place, if desired, in hours or even longer, after the radiolabeled reagent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-99m labeled reagents and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of BAT Chelators

A. Synthesis of N-Boc-N'-(5-carboxypentyl)-N,N'-bis(2-methyl-2-triphenylmethylthiopropyl)ethylenediamine a. Synthesis of 2-methyl-2-(triphenylmethylthio)propanal Triphenylmethylmercaptan (362.94 g, 1.31 mol, 100 mol %) dissolved in anhydrous THF (2 L) was cooled in an ice bath under argon. Sodium hydride (60% in oil; 54.39 g, 1.35 mol, 104 mol %) was added in portions over 20 min. 2-bromo-2-methylpropanal (206.06 g, 1.36 mol, 104 mol %; see Stevens & Gillis, 1957, J. Amer. Chem. Soc. 79: 3448–51) was then added slowly over 20 min. The reaction mixture was allowed to warm to room temperature and stirred for 12 hours. The reaction was quenched with water (1 L) and extracted with diethyl ether (3×1 L). The ether extracts were combined, washed with saturated NaCl solution (500 mL), dried over $Na_2SO_4$ and filtered. The solvent was removed under reduced pressure to afford a thick orange oil. The crude oil was dissolved in toluene (200 mL) and diluted to 2 L with hot hexanes. The mixture was filtered through a sintered glass funnel and cooled at −5° C. for 12 hours. The white crystalline solid which formed was removed by filtration to afford 266.36 g (59% yield) of the title compound. The melting point of the resulting compound was determined to be 83–85° C. Nuclear magnetic resonance characterization experiments yielded the following molecular signature:

$^1$H NMR(300 $MH_z$, $CDCl_3$): δ 1.24(s, 6H, $2CH_3$), 7.2–7.35 (m, 9H), 7.59– 7.62 (m,6H), 8.69 (s, H, —COH)
$^{13}$C NMR (75 MHz, $CDCl_3$): δ 22.86, 55.66, 67.48, 126.85, 127.75, 129.72, 144.79, 197.31.

b. Synthesis of N,N'-bis(2-methyl-2-triphenylmethylthiopropyl) ethylenediamine

Ethylenediamine (1.3 mL, 0.0194 mol, 100 mol %) was added to 2methyl-2-(triphenylmethylthio)propanal (13.86 g, 0.0401 mol, 206 mol %) dissolved in methanol (40 mL) and anhydrous THF (40 mL) under argon, and the pH was adjusted to pH 6 by dropwise addition of acetic acid. The solution was stirred for 20 min at 20° C. Sodium cyanoborohydride (1.22 g, 0.0194 mol, 100 mol %) was added and the reaction was stirred at room temperature for 3 hours. Additional sodium cyanoborohydride (1.08 g) was added and the reaction was stirred at 20° C. for 17 hours. A final portion of sodium cyanoborohydride (1.02 g) was added and the reaction heated at reflux under argon for 6 hours. The reaction was quenched with 0.5 M HCl (100 mL) and extracted with ethyl acetate (2×100 mL). The organic extracts were combined, sequentially washed with 2 M NaOH (60 mL), saturated NaCl solution (60 mL), dried ($Na_2SO_4$), and filtered. The solvent was removed under reduced pressure to give 16.67 g of crude product which was crystallized from toluene/hexanes to afford 10.20 g (73% yield) of white crystals of the title compound. The melting point of the resulting compound was determined to be 83–86° C. FABMS analysis yielded an m/z of 721 (MH+). Nuclear magnetic resonance characterization experiments yielded the following molecular signature:
$^1$H NMR (300 MH$_z$, CDCl$_3$): δ 1.12 (s, 12H, 4 CH$_3$), 1.64 (s, 4H, N—CH$_2$—C(Me)$_2$—S), 2.52 (s, 4H, N—CH$_2$—CH$_2$—N), 5.31 (S, 2H, 2-NH), 7.12–7.30 (m, 18H, Ar), 7.62–7.65 (m, 12H, Ar).

c. Synthesis of N-(5-carboethoxypentyl)-N,'-bis(2-methyl-2triphenylmethylthiopropyl)ethylenediamine K$_2$CO$_3$ (1.92 g, 13.9 mmol, 100 mol %) was added to N,N'-bis(2-methyl-2-triphenylmethylthiopropyl) ethylenediamine (10.03 g, 13.9 mmol) in CH$_3$CN (60 mL), followed by ethyl 5-bromovalerate (3.30 mL, 20.8 mmol, 150 mol %). The reaction was heated at reflux under argon overnight. The solution was then concentrated to a paste and partitioned between 0.25 M KOH (100 mL) and ethyl acetate (100 mL). The aqueous layer was extracted with ethyl acetate (1×50 mL) and the combined ethyl acetate layers were washed with 50 mL water and NaCl solution (2×50 mL), dried with Na$_2$SO$_4$ and concentrated to an orange oil. Purification by flash chromatography (300 g flash silica, 100% CHCl$_3$ to 5% MeOH/CHCl$_3$) gave pure title compound (7.75 g, 66% yield). FABMS analysis yielded an (MH+) of 849 (compared with a calculated molecular weight of 849.24 for the compound C$_{55}$H$_{64}$N$_2$O$_2$S$_2$).

d. Synthesis of N-Boc-N'-(5-carboxypentyl)-N,N'-bis(2-methyl-2-triphenylmethylthiopropyl)ethylenediamine 1M KOH (25 mL, 25.0 mmol, 274 mol %) was added to N-(5carboethoxypentyl)-N,N'-bis(2-methyl-2-triphenylmethylthiopropyl) ethylenediamine (7.75 g, 9.13 mmol) in dioxane (200 mL), followed by water (250 mL). Dioxane was then added dropwise with stirring until a homogeneous solution was obtained. The reaction was heated at a slow reflux overnight. Most of the dioxane was removed by rotary evaporation and the pH of solution was adjusted to ~7–8 with 1 M KH$_2$PO$_4$ and saturated NaHCO$_3$. The solution was then extracted with ethyl acetate (3×75 mL) and the combined organic layers were washed with NaCl solution (50 mL), dried with Na$_2$SO$_4$ and concentrated to a foam/solid (6.35 g, 85% yield).

To the crude product from the above reaction was added (BOC)$_2$O (3.35 g, 15.4 mmol, 200 mol %), CH$_3$CN (50 mL) and methylene chloride (50 mL), followed by triethylamine (1.0 mL, 7.2 mmol, 93 mol %). The reaction was stirred at room temperature under argon overnight. The reaction solution was then concentrated and partitioned between water (100 mL) and ethyl acetate (50 mL). The aqueous layer was extracted with ethyl acetate (1×50 mL) and the combined ethyl acetate layers were washed with 5% citric acid and NaCl solution (50 mL each), then dried (Na$_2$SO$_4$) and concentrated to an orange oil. Purification by flash chromatography (200 g flash silica, 100% CDCl$_3$ to 5% methanol/chloroform) gave pure title compound N-Boc-N'-(5-carboxypentyl)-N,N'-bis(2-methyl-2-triphenylmethylthiopropyl)ethylenediamine (2.58 g, 36% yield). FABMS analysis gave an (MH+) of 921 (compared with the calculated value of 921.31 for the compound C$_{58}$H$_{68}$N$_2$O$_4$S$_2$).

B. Synthesis of N-Boc-N'-(5-carboxypentyl)-N,N'-bis-[2-(4-methoxybenzylthio)-2-methylpropyl]ethylenediamine a. Synthesis of N,N'-bis-[2-(4-methoxybenzylthio)-2-methylpropyl]ethylenediamine A solution of N,N'-bis(2-mercapto-2-methylpropyl) ethylenediamine (11.23 g, 47.5 mmol; see, DiZio et al., 1991, Bioconjugate Chem 2: 353 and Corbin et al., 1976, J. Org. Chem. 41: 489) in methanol (500 mL) was cooled in ice/water bath and then saturated with gaseous ammonia over 45 min. To this was added 4-methoxybenzyl chloride (17.0 mL, 125 mmol, 264 mol %). The reaction was allowed to warm to room temperature overnight with stirring under argon. The solution was concentrated to a paste and then partitioned between diethyl ether (150 mL) and 0.5 M KOH (200 mL). The aqueous layer was further extracted with diethyl ether (2×50 mL). The combined organic layers were washed with NaCl solution and concentrated to a clear colorless oil. The oil was dissolved in diethyl ether (200 mL) and then acidified with 4.0 M HCl in dioxane until no further precipitation was seen. The white precipitate was collected by filtration and washed with diethyl ether. The white solid was recrystallized from hot water at a pH of ~2. The product was collected by filtration to afford 29.94 g as a mix of mono- and di-HCl salts. The HCl salts were partitioned between 1 M KOH (100 mL) and ethyl acetate (100 mL). The aqueous was extracted with ethyl acetate (2×30 mL) and the combined organic layers were washed with NaCl solution, dried with Na$_2$SO$_4$ and concentrated to give pure product as the free base as a light yellow oil (18.53 g, 82% yield). Nuclear magnetic resonance characterization experiments yielded the following molecular signature:
$^1$H NMR (300 MHz, CDCL$_3$): δ 7.25 (d, 4H, J=9), 6.83 (d, 4H, J=9), 3.78 (s, 6H), 3.67 (s, 4H), 2.63 (s, 4H), 2.56 (s, 4H), 1.34 (s, 12H).

b. SynthesisofN-(5-carboethoxypentyl)-N,N'-bis-[2-(4-methoxybenzylthio)-2methylpropyl]ethylenediamine To N,N'-bis-[2-(4-methoxybenzylthio)-2-methylpropyl]-ethylenediamine (4.13 g, 8.66 mmol) in CH$_3$CN (50 mL) was added K$_2$CO$_3$ (1.21 g, 8.75 mmol, 101 mol %) followed by ethyl 5-bromovalerate (2.80 mL, 17.7 mmol, 204 mol %). The reaction was stirred at reflux overnight and was then concentrated to a paste in vacuo. The residue was partitioned between ethyl acetate (100 mL) and 0.5 M KOH (100 mL). The aqueous layer was extracted with ethyl acetate (1×50 mL) and the combined organic layers were washed with NaCl solution (50 mL), dried with Na$_2$SO$_4$ and concentrated to a yellow oil (~6 g). Purification by normal-phase preparative HPLC (100% CHCl$_3$ to 5% methanol/chloroform over 25 min.) afforded pure title compound (1.759 g, 34% yield). FABMS analysis gave an (MH+) of 605 (compared with the value of 604.90 calculated for C$_{33}$H$_{52}$N$_2$O$_4$S$_2$). Nuclear magnetic resonance characterization experiments yielded the following molecular signature:
$^1$H NMR (300 mH,, CDCl$_3$): δ 7.25 (d, 4H, J=8.5), 6.83 (d, 4H, J=8.5), 4.13 (q, 2H, J=7), 3.793 (s, 3H), 3.789 (s. 3H), 3.74 (s, 2H), 3.67 (s, 2H), 2.6 (m, 10H), 2.31 (t, 2H, J=7), 1.6 (m, 2H), 1.5 (m 2H), 1.34 (s 12H), 1.28 (t, 3H, J=7).

c. Synthesis of N-Boc-N'-(5-carboxypentyl)-N,N'-bis-[2-(4-methoxybenzylthio)-2-methylpropyl]ethylenediamine To N-(5-carboethoxypentyl)-N,N'-bis-[2-(4-methoxybenzylthio)-2methylpropyl]ethylenediamine (586 mg, 0.969 mmol) in THF (40 mL) was added water (30 mL)

and 1 M KOH (2.5 mL, 2.5 mmol, 260 mol %). The homogeneous solution was heated to a slow reflux overnight. The solution was then cooled to room temperature and the THF was removed under rotary evaporation. The residue was diluted to 50 mL with $H_2O$ and the pH was adjusted to ~2–3 with 1 M HCl. The solution was extracted with ethyl acetate (3×30 mL) and the combined organic layers were washed with NaCl solution (50 mL), dried with $Na_2SO_4$ and concentrated to give crude acid (422 mg, 75% yield).

To the crude product from the above reaction was added $CH_3CN$ (40 mL) and $(BOC)_2O$ (240 mg, 1.10 mmol, 150 mol %) followed by triethylamine (0.200 mL, 1.43 mmol, 196 mol %). The homogenous solution was stirred at room temperature overnight under argon. The solution was then concentrated to a paste and partitioned between ethyl acetate (25 mL) and 1 M $KH2PO_4$ (25 mL). The organic layer was washed with 5% citric acid (2×25 mL) and NaCl solution (25 mL), dried with $Na_2SO_4$ and concentrated to a yellow oil. Purification by flash chromatography (50 mL flash silica gel, 100% chloroform to 15% methanol/chloroform) gave pure title compound N-Boc-N'-(5carboxypentyl)-N,N'-bis-[2-(4-methoxybenzylthio)-2-methylpropyl] ethylenediamine (344 mg, 70% yield). FABMS analysis gave an (MH+) of 677 (compared to the value of 676.97 calculated for the compound $C_{36}H_{56}N_2O_6S_2$). Nuclear magnetic resonance characterization experiments yielded the following molecular signature:

$^1$H NMR (300 MHz, $CDCl_3$): δ 7.20 (d, 4H, J=7), 6.79 (d, 4H, J=7), 3.75 (S, 3H), 3.74 (S, 3H), 3.68 (M, 4H), 3.35 (M, 4H), 2.65 (M, 2H), 2.53 (M, 4H), 2.31 (M, 2H), 1.59 (M, 2H), 1.43 (S, 11H), 1.30 (S, 6H), 1.26 (S, 6H)

C. Synthesis of BAT-BM (N-[2-(N',N'-bis(2-maleimidoethyl)aminoethyl)]-$N^6$,$N^9$-bis(2methyl-2-triphenylmethylthiopropyl)-6,9-diazanonanamide)

BAT-BM was prepared as follows. BAT acid ($N^9$-(t-butoxycarbonyl)-$N^6$,$N^9$-bis(2-methyl-2-triphenylmethylthiopropyl)-6,9-diazanonanoicacid) (10.03 g, 10.89 mmol) and 75 mL of dry methylene chloride ($CH_2Cl_2$) were added to a 250 mL round-bottomed flask equipped with magnetic stir bar and argon balloon. To this solution was added diisopropylcarbodiimide (3.40 mL, 21.7 mmol, 199 mole %), followed by N-hydroxy-succinimide (3.12 g, 27.1 mmol, 249 mole %). This solution was observed to become cloudy within 1 h, and was further incubated with stirring for a total of 4h at room temperature. A solution of tris(2-aminoethyl)amine (30 mL, 200 mmol, 1840 mole %) in 30 mL methylene chloride was then added and stirring continued overnight. The reaction mixture was then concentrated under reduced pressure, and the residue partitioned between ethylacetate (150 mL) and 0.5M potassium carbonate ($K_2CO_3$; 150 mL). The organic layer was separated, washed with brine and concentrated to give the crude product N-[2-(N',N'-bis(2-aminoethyl)aminoethyl)]-$N^9$-(t-butoxycarbonyl)-$N^6$,$N^9$-bis(2-methyl-2-triphenylmethylthiopropyl)-6,9-diazanonanamide as a foam/oil.

This crude product was added to a 1000 mL round-bottomed flask, equipped with magnetic stir bar, containing 300 mL THF, and then 30 mL saturated sodium bicarbonate ($NaHCO_3$), 100 mL water and N-methoxycarbonylmaleimide (6.13 g, 39.5 mmol, 363 mole %) were added. This heterogeneous mixture was stirred overnight at room temperature. THF was removed from the mixture by rotary evaporation, and the aqueous residue was twice extracted with ethylacetate (2×75 mL). The combined organic layers of these extractions were washed with brine, dried over sodium sulfate, filtered through a medium frit and concentrated to about 12 g of crude product. Purification by liquid chromatography (250 g silicon dioxide/eluted with a gradient of chloroform 2% methanol in chloroform) afforded 5.3 g of pure product (N-[2-(N', N'-bis(2-maleimidoethyl)aminoethyl)]-$N^9$-(t-butoxycarbonyl)-$N^6$,$N^9$-bis(2-methyl-2-triphenylmethylthiopropyl)-6,9-diazanonanamide (equivalent to 40% yield), along with approximately 5 g of crude product that can be re-purified to yield pure product. Chemical analysis of the purified product confirmed its identity as BAT-BM as follows:

$^1$H NMR (200 mHz, $CDCl_3$): δ 0.91 (12H,s), 1.38 (9H,s), 1.2–1.6 (4H,m), 2.06 (2H,s), 2.18 (2H,t,J=7), 2.31 (4H,m), 2.55 (2H,t,J=5), 2.61 (4H,t,J=6), 2.99 (2H,s), 3.0–3.3 (4H, m), 3.46 (4H,t,J=6), 6.49 (—NH,t,J=4), 6.64 (4H,s), 7.1–7.3 (18H,m), 7.6 (12H,t,J=17).

D. Synthesis of [BAT]-conjugated(εN) Lys(αN-Fmoc) [N-ε-($N^9$-t-butoxycarbonyl)-$N^6$,$N^9$-bis[2-methyl-2-(triphenylmethylthio)propyl]-6,9-diazanonanoyl)-N-α-Fmoc-lysine A 100 mL single-necked round-bottomed flask, equipped with stir bar and argon balloon, was charged with $N^9$-(t-butoxycarbonyl)-$N^6$,$N^9$-bis[2-methyl-2-(triphenylmethylthio)propyl]-6,9-diazanonanoic acid (BAT acid; 3.29 g, 3.57 mmol) in 50 mL $CH_2Cl_2$ at room temperature. To this was added diisopropylcarbodiimide (DIC; 580 μL, 3.70 mmol, 104 mole %) followed immediately by N-hydroxysuccinimide (HOSu; 432 mg, 3.75 mmol, 105 mole %). The reaction was stirred overnight at room temperature during which time a white precipitate developed. The mixture was filtered and the filtrate concentrated to a solid foam. The crude foam, in a 100 mL round-bottomed flask, was dissolved in 75 mL of a 2:1 mixture of dimethoxyethane and water. To this homogeneous solution was added N-a-Fmoc-lysine hydrochloride (1.52 g, 3.75 mmol, 105 mole %) followed by $K_2CO_3$ (517 mg, 3,74 mmol, 105 mole %), and the yellow solution stirred overnight at room temperature. The solution was then poured into a 250 mL erlenmeyer flask containing 100 mL of ethyl acetate and 100 mL of water. The organic layer was separated and the aqueous layer further extracted with 50 mL ethyl acetate. The combined organic layers were washed once with brine (100 mL), dried over $Na_2SO_4$ and concentrated to a yellow solid. This crude product was purified by low-pressure liquid chromatography (150 g $SiO_2$, eluted with $CHCl_3$→10% methanol in $CHCl_3$). In this way, 3.12 g of the named compound was prepared (69% yield). Chemical analysis of the purified product confirmed its identity as follows:

$^1$H NMR (300 MHz, $CDCl_3$): δ 0.88 (12H,s,broad), 1.05–1.45 (19H,m), 1.8–2.1 (4H,m), 1.8–2.47 (4H,m), 2.75–3.2 (6H,m), 3.9–4.3 (4H,m,), 7.2 (22H,m), 7.6 (16H, s,bound). FABMS $MH^+$ was predicted to be 1270.6 and found to be 1272.

E. Synthesis of BAM ($N^1$-(t-butoxycarbonyl)-$N^1$,$N^4$-bis[2-methyl-2-(triphenylmethylthio)propyl]-1,4,10-triazadecane A 250 mL single-necked round-bottomed flask, equipped with a stir bar, reflux condenser and argon balloon, was charged with $N^1$,$N^4$-bis[2-methyl-2-(triphenylmethylthio)

propyl]-ethylenediamine (BAT-I; 10.0 g, 14.01 mmol) in 50 mL of $CH_3CN$ and 30 mL dioxane. To this was added N-(5-bromopentyl)-phthalimide (8.04 g, 27.1 mmol, 194 mole %) followed by $K_2CO_3$ (2.95 g, 21.3 mmol, 152 mole %). The mixture was heated at reflux under argon for two days. The reaction mixture was then concentrated and the residue partitioned between 150 mL water and 150 mL ethyl acetate. The organic layer was separated and the aqueous layer (at pH of about 10) was further extracted with 50 mL ethyl acetate. The combined organic layers were washed once with brine (75 mL), dried over $Na_2CO_3$ and concentrated to an oil. Purification by low-pressure liquid chromatography (300 g $SiO_2$, $CHCl_3 \rightarrow 2\%$ methanol in $CHCl_3$) afforded 9.20 g of 9-phthalimido-$N^1,N^4$-bis[2-methyl-2-(triphenylmethylthio)propyl]-1,4-diazanonane as a yellow foam (70% yield). Chemical analysis of the purified product of this intermediate confirmed its identity as follows:

$^1$H NMR (300 MHz, $CDCl_3$): δ 1.01 (6H,s), 1.03 (6H,s), 1.15–1.4 (2H,t), 1.98 (2H,s), 2.10 (2H,s), 2.28 (2H,m), 2.45 (3H,m), 3.68 (2H,t), 7.15–7.35 (18H, m), 7.62 (12H, t), 7.72 (2H, m), 7.85 (2H,m). FABMS $MH^+$ was predicted to be 935.4 and found to be 936.

A 500 mL single-necked round-bottomed flask, equipped with stir bar, was charged with 9-phthalimido-$N^1,N^4$-bis[2-methyl-2-(triphenylmethylthio)propyl]-1,4-diazanonane (8.83 g, 9.43 mmol) in 75 mL of $CH_3CN$ and 20 mL $CH_2Cl_2$. To this was added $K_2CO_3$ (1.30 g, 9,41 mmol, 100 mole %), followed by di-tert-butyl dicarbonate (2.15 g, 9.85 mmol, 104 mole %), and the reaction stirred at room temperature overnight. The reaction mixture was then concentrated and partitioned between 100 mL each of water and ethyl acetate. The organic layer was separated and the aqueous layer was further extracted with 50 mL ethyl acetate. The combined organic layers were washed once with brine (75 mL), dried over $Na_2SO_4$ and concentrated to give 9.69 g of crude 9-phthalimido-N'-(t-butoxycarbonyl)-$N^1,N^4$-bis[2-methyl-2-(triphenylmethylthio)propyl]-1,4-diazanonane as a yellow foam (99% crude yield). This crude product was used without further purification.

A 250 mL single-necked round-bottomed flask, equipped with stir bar and reflux condenser, was charged with 9-phthalimido-$N^1$-(t-butoxycarbonyl)-$N^1,N^4$-bis[2-methyl-2-(triphenylmethylthio)propyl]-1,4-diazanonane (5.50 g, 5.319.43 mmol) in 25 mL of THF. To this was added 100 mL ethanol and 5 mL water. The addition of water caused the starting material to precipitate out of solution. Hydrazine hydrate (1.2 mL, 24.7 mmol, 466 mole %) was added, and the reaction heated at reflux for two days. The reaction mixture was concentrated and partitioned between 100 mL each of water and 0.25M $K_2CO_3$. The organic layer was separated and washed once with brine (75 mL), dried over $Na_2SO_4$ and concentrated to a solid foam. Purification of the crude product by low-pressure liquid chromatography (100 g $SiO_2$, $CHCl_3 \rightarrow 5\%$ methanol in $CHCl_3$, the column pre-treated with 200 mL 2% triethylamine in $CHCl_3$) afforded 3.27 g of pure N'-(t-butoxycarbonyl)-$N^1,N^4$-bis[2-methyl-2-(triphenylmethylthio)propyl]-1,4,10-triazadecane as a yellow foam (68% yield). Chemical analysis of the purified product confirmed its identity as follows:

$^1$H NMR (300 MHz, $CDCl_3$): δ 0.9 (12H,s), 1.2 (6H,s), 1.36 (9H,s), 2.05 (4H,m), 2.24 (2H,t), 2.31 (2H,t), 2.62 (3H,t), 3.0 (2H,s,broad), 3.1 (2H,s,broad), 7.2 (18H,m), 7.6 (12H,t). FABMS $MH^+$ was predicted to be 905.5 and found to be 906.5.

EXAMPLE 2

Synthesis of Polyvalent Linking Moieties

1. Synthesis of TMEA [tris(2-maleimidoethyl)amine]

tris(2-aminoethyl)amine (1.49 mL, 10 mmol) dissolved in 50 mL saturated aqueous sodium bicarbonate and cooled in an ice bath, was treated with N-carbomethoxymaleimide (4.808 g, 31 mmol). The mixture was stirred for 30 min on ice and then for another 30 min at room temperature. The mixture was then partitioned between dichloromethane and water, dried over magnesium sulfate, filtered and evaporated to give 3.442 g of product. Reverse phase thin-layer chromatography (RP-TLC) yielded essentially 1 spot ($R_f$=0.63 in 1:1 acetonitrile: 0.5 M sodium chloride). 3.94 mmol (1.817 g) of this product was dissolved in 20 mL tetrahydrofuran and 20 mL saturated sodium bicarbonate and mixed for 2 h. The reaction mixture was then partitioned between ethyl acetate and water. The organic phase was washed with saturated sodium chloride, dried over magnesium sulfate, and filtered. The ethyl acetate solution was diluted with hexanes and cooled. Solid TMEA was collected by filtration and dried to a yield of 832 mg. Chemical analysis of the product confirmed its identity as TMEA as follows:

$^1$H NMR ($CDCl_3$): 2.65 (tr. 2 H), 3.45 (tr.2H). 6.64 (s. 2H).
$^{13}$C NMR ($CDCl_3$), 35.5, 51.5, 133.9, 170.4.

2. Synthesis of TMEB (4-[1-(2-tolylsulfonylmethyl) ethenylcarbonyl]benzoic acid)

4-(bis-(2-toluenethiomethyl)acetyl)benzoic acid was prepared from 2thiocresol using the methods of Lawton and co-workers (1990, Bioconjugate Chemistry 1: 36). The identity of the resulting compound was established by chemical analysis as follows:

FABMS: $MH^+$=436.
$^1$H NMR ($CDCl_3$)=2.62 (s, 6H), 3.2–3.4 (m, 4H), 3.94 (d tr, 1H), 7.10–7.26 (m, 8H), 7.64 (d, 2H), 8.07 (d, 2H). $^3$C NMR ($CDCl_3$): 20.2, 34.9, 45.4, 126.5, 126.8, 128.1, 129.9, 130.3, 130.4, 132.9, 133.9, 138.9, 140.5.

To a solution of 4-(bis-(2-toluenethiomethyl)acetyl) benzoic acid (1.865 g, 4.27 mmol) in 50% methanol/water (12.5 mL) was added acetic acid (2.69 mL) followed by 30% hydrogen peroxide (2.61 mL) and disodium tungstate dihydrate (0.187 g, 0.56 mmol). The mixture was stirred overnight and the crude product was filtered off. Recrystallization from methanol/water and reverse-phase HPLC (0.1% $CF_3COOH$/acetonitrile/water) gave TMEB (178 mg). The identity of the resulting compound was established by chemical analysis as follows:

$^1$H NMR (DMSO-d6): 2.68 (s, 3H), 4.56 (s, 2H), 5.95 (s. 1H), 6.27 (s. 1H), 7.37–8.05 (m, 8H).

EXAMPLE 3

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxy-methylpolystyrene (HMP) resin for carboxyl-terminus acids or Rink amide resin for carboxyl-terminus amides. Resin-bound products were routinely cleaved for 1.5–3 h at room temperature using a solution comprised of trifluoroacetic acid, optionally comprising water, thioanisole, ethanedithiol, and triethylsilane in ratios of 100:5:5:2.5:2.

Where appropriate, N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/diisopropylethylamine in NMP. Where appropriate, 2-haloacetylated peptides were cyclized by stirring an 0.1–1.0 mg/mL solution in phosphate or bicarbonate buffer (pH 8) containing 0.5–1.0 mM EDTA for 4–48 hours, followed by acidification with acetic acid, lyophilization and HPLC purification. Where appropriate, Cys—Cys disulfide bond cyclizations were performed by treating the precursor cysteine-free thiol peptides at 0.1 mg/mL in pH 7 buffer with aliquots of 0.006M $K_3Fe(CN)_6$ until a stable yellow color persisted. The excess oxidant was reduced with excess cysteine, the mixture lyophilized and then purified by HPLC.

Where appropriate the "Pic" group was introduced by using picolinic acid as the last residue in peptide synthesis. Where appropriate the "Pica" group was introduced by conjugating picolylamine to a precursor peptide using diisopropylcarbodiimide and N-hydroxysuccinimide. Where appropriate BAT ligands were introduced either by using the appropriate BAT acid as the last residue to be coupled during SPPS or by treating the N-terminus free amino peptide bound to the resin with BAT acid/diisopropylcarbodiimide/N-hydroxysuccinimide in NMP. Where appropriate, [BAM] was conjugated to the peptide by first activating the peptide carboxylate with a mixture of diisopropylcarbodiimide/N-hydroxysuccinimide or HBTU/HOBt in DMF, NMP or $CH_2Cl_2$, followed by coupling in the presence of diisopropylethylamine; after coupling, the conjugate was deprotected as described above.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) predissolved in acetonitrile at room temperature for approximately 1–18 hours. The solution was concentrated and the product was purified by HPLC. Where appropriate, BSH adducts were prepared by using bis-maleimidohexane in place of BMME.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/acetonitrile or THF) with 0.33 molar equivalents of TMEA (tris(2-maleimidoethyl)amine; see co-pending U.S. patent application Ser. No. 07/955,466, incorporated by reference) predissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-[2-(N',N'-bis(2-maleimidoethyl)aminoethyl)]-$N^9$-(t-butoxycarbonyl)-$N^6$,$N^9$-bis(2-methyl-2-triphenylmethylthiopropyl)-6,9-diazanonanamide; see co-pending U.S. patent application Ser. No. 08/044,825, incorporated by reference) predissolved in acetonitrile or THF, at room temperature for approximately 1–18 h. The solution was then evaporated to dryness and [BAT-BS]-peptide conjugates deprotected by treatment with 10 mL TFA and 0.2 mL triethylsilane for 1 h. The solution was concentrated, the product adducts precipitated with ether, and then purified by HPLC.

Where appropriate, DMAB adducts were prepared by reacting single thiol-containing peptides (10 to 100 mg/mL in DMF) with 0.5 molar equivalents of TMEB (described in Example 2) and 1 molar equivalent of triethanolamine at room temperature for approximately 12 to 18 hours. DMF was then removed in vacuo and the product purified by HPLC.

Crude peptides were purified by preparative high pressure liquid chromatography (HPLC) under conditions described in the footnotes to Table I below. Eluted fractions which were then lyophilized, and the identity of each product was confirmed by fast atom bombardment mass spectroscopy (FABMS) or electrospray mass spectroscopy (ESMS).

EXAMPLE 4

A General Method for Radiolabeling with Tc-99m 0.1 mg of a peptide reagent prepared as in Example 3 was dissolved in 0.1 mL of water, or 50:50 ethanol:water, or phosphate-buffered saline (PBS), or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the reagent and the reaction allowed to proceed at room temperature or at 100° C. for 15–30 min and then filtered through a 0.2 μm filter.

The Tc-99m labeled peptide reagent purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 3 using the method described herein.

TABLE I

| Peptides | FABMS MH+ | Radiochemical Yield(%)* | HPLC R$_T$(min)** |
|---|---|---|---|
| (acetyl.F$_D$PRPG)$_2$KGGGCamide | 1613 | 98$^2$ | 17.4$^3$ |
| (GPRVVERHQSA)$_2$KC$_{Acm}$GC$_{Acm}$amide | 2986 | 99$^3$ | 16.0$^3$ |
| [(GRP)$_2$K]$_2$KC$_{Acm}$GC$_{Acm}$amide | 2437 | 100$^3$ | 16.3$^3$ |
| (CH$_3$CO.Y$_D$.Apc.GDCGGC$_{Acm}$GC$_{Acm}$GGCamide)$_2$-BSME | 3021 | N.D. | N.D. |
| (CC$_{Acm}$GC$_{Acm}$GGRGDS)$_3$-TSEA | ND | 82$^1$ | 10.4$^3$ |
| (GPRPC$_{Acm}$GC$_{Acm}$Camide)$_3$-TSEA | 3189 | 93$^1$ | 10.0$^3$ |
| (Pic.SC$_{Acm}$SYNRGDSTCamide)$_3$-TSEA | 4489 | 99$^1$ | 10.4, 11.2$^3$ |
| (RALVDTKGGC$_{Acm}$GC$_{Acm}$Camide)$_3$-TSEA | 4998 | 95$^2$ | 13.4, 13.7$^3$ |
| (GRGDFC$_{Acm}$GC$_{Acm}$Camide)$_3$-TSEA | 3561 | N.D. | N.D. |
| (acetyl.SYNRGDTC$_{Acm}$GC$_{Acm}$Camide)$_2$-DMAB | 3087 | N.D. | N.D. |
| (Pic.GC$_{Acm}$RALVDTLKFVTQAEGAKCamide)$_3$-TSEA | 7243 | 98$^4$ | 18.3, 19.0$^3$ |
| (CH$_3$CO.Y$_D$.Apc.GDCGGC$_{Acm}$GC$_{Acm}$GGCamide)$_3$-TSEA | 4586 | 99$^3$ | 9.2, 11.6$^1$ |
| (formyl.MLFK(N$_\epsilon$-BAT)GGC$_{Acm}$GC$_{Acm}$GGC.amide)$_2$-BSME | 3477 | 99$^2$ | 11.9, 12.4$^1$ |
| (CH$_3$CO.Y$_D$.Apc.GDCKGC$_{Acm}$GC$_{Acm}$GGCamide)$_2$-BSME | 3163 | 98$^3$ | 9.6$^1$ |
| (acetyl.CC$_{Acm}$GC$_{Acm}$PLYKKIIKKLLES)$_2$-BSME | 4483 | 98$^3$ | 11.6$^1$ |
| (GPRPPPGGC$_{Acm}$GC$_{Acm}$GGCamide)$_3$-TSEA | 4454$^z$ | 100$^3$ | 9.1$^1$ |
| (ma.GGGRALVDTLKFVTQAEGAKamide)$_2$-[BAT-BS] | 4808 | 96 | 12.0$^3$ |
| (CH$_3$CO.Y$_D$.Apc.GDCGGC$_{Acm}$GC$_{Acm}$GGCamide)$_2$-BSH | 3062 | 100$^3$ | 11.5$^2$ |
| (CH$_3$CO.Y.Apc.GDCKGC$_{Acm}$GC$_{Acm}$GGCamide)$_2$-[BAT-BS] | 3552 | N.D. | N.D. |
| (acetyl.CC$_{Acm}$GC$_{Acm}$GGPLYKKIIKKLLES)$_2$-BSME | 4825$^z$ | 99$^3$ | 16.2$^1$ |
| (CH$_3$CO.Y$_D$.Apc.GDCGGC$_{Acm}$GC$_{Acm}$GGCamide)$_2$-[BAT-BS] | 3409$^z$ | 98$^2$ | 10.3$^1$ |

N.D. = not determined; z = molecular weight determined by electrospray mass spectroscopy (ESMS)
*Superscripts refer to the following labeling conditions:
1. The peptide is dissolved in 50 mM potassium phosphate buffer (pH 7.4) and labeled at 100° C.
2. The peptide is dissolved in water and labeled at room temperature.
3. The peptide is dissolved in water and labeled at 100° C.
4. The peptide is dissolved in a 50:50 mixture comprising 50 mM potassium phosphate buffer (pH 7.4) and absolute ethanol and labeled at 100° C.
**HPLC methods (indicated by superscript after R$_T$):
general:
solvent A = 0.1% CF3COOH/H$_2$O
solvent B$_{90}$ = 0.1% CF$_3$COOH/90% CH$_3$CN/H$_2$O
solvent flow rate = 1 mL/min
Vydak column = Vydak 218TP54 RP-18, 5$\mu$ × 220 mm × 4.6 mm analytical column with guard column
Waters column = Waters DeltaPak C18, 5$\mu$ × 150 mm × 3.9 mm column
Conditions:
1. 100% A to 100% B$_{90}$ in 10 min, Waters column
2. 100% A to 100% B$_{90}$ in 20 min, Waters column
3. 100% A to 100% B$_{90}$ in 10 min, Vydak column Single-letter abbreviations for amino acids can be found in G. Zubay, *Biochemistry* (2d. ed.), 1988 (MacMillen Publishing: New York) p.33. Underlining indicates the formation of a thiol linkage between the linked amino acids of derivative groups; peptides are linked to BSH, DMAB, BSME, TSEA or [BAT-BS] linkers via the free thiol moiety of the unprotected cysteine residue (C) in each such peptide. Pic is picolinoyl (pyridine-2-carbonyl); Acm is acetamidomethyl; Apc is L-[S-(3-aminopropyl)cysteine; F$_D$ is D-phenylalanine; Y$_D$ is D-tyrosine; K(N$_l$-BAT) is a lysine covalently linked to a BAT moiety via the ε-amino group of the sidechain; ma is 2-mercaptoacetic acid; BAT is N$^6$,N$^9$-bis(2-mercapto-2-methylpropyl)-6,9-diazanonanoic acid; BAT-BS is N-[2-N',N'-bis(2-succinimidoethyl)aminoethyl]-N$^6$,N$^9$-bis(2-mercapto-2-methylpropyl)-6,9-diazanonanamide; BSME is bis-succinimidomethylether; TSEA is tris-(2-succinimidoethyl)amine; BSH is 1,6-bis-succinimidohexane; and DMAB is 4-(2,2-dimethylacetyl) benzoic acid. Chemical structures of the reagents of the invention are as follows:

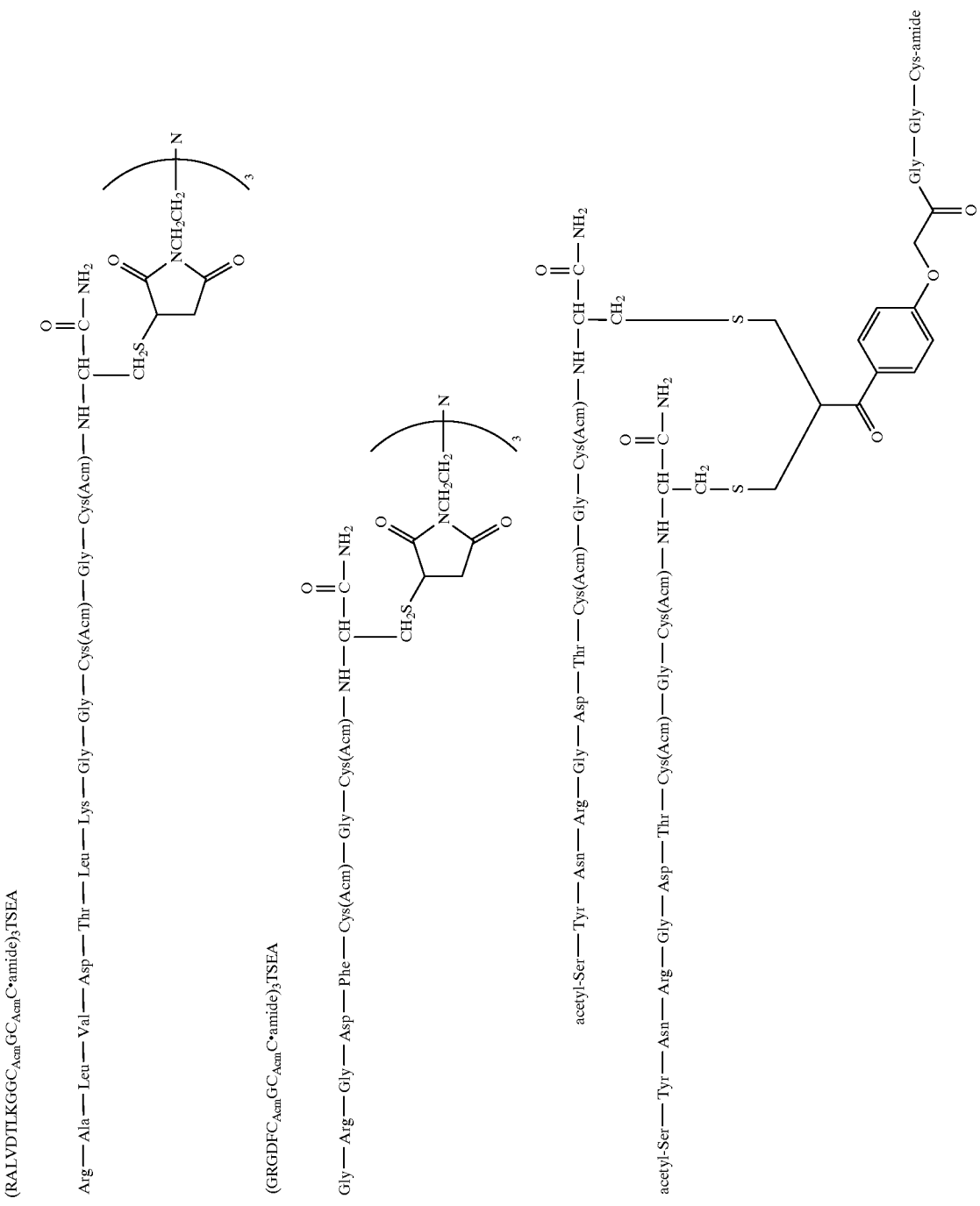

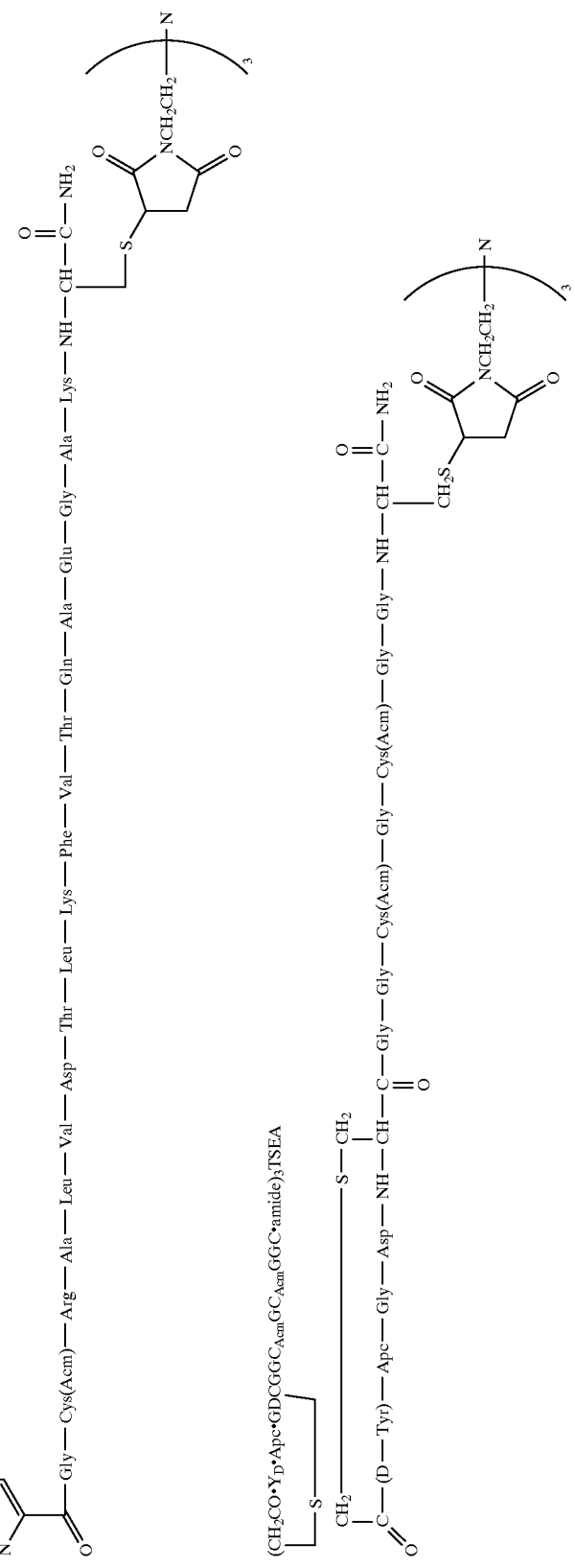
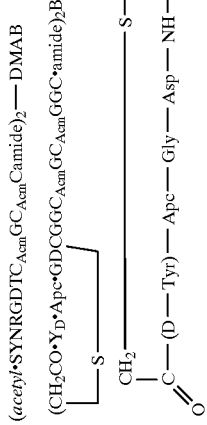

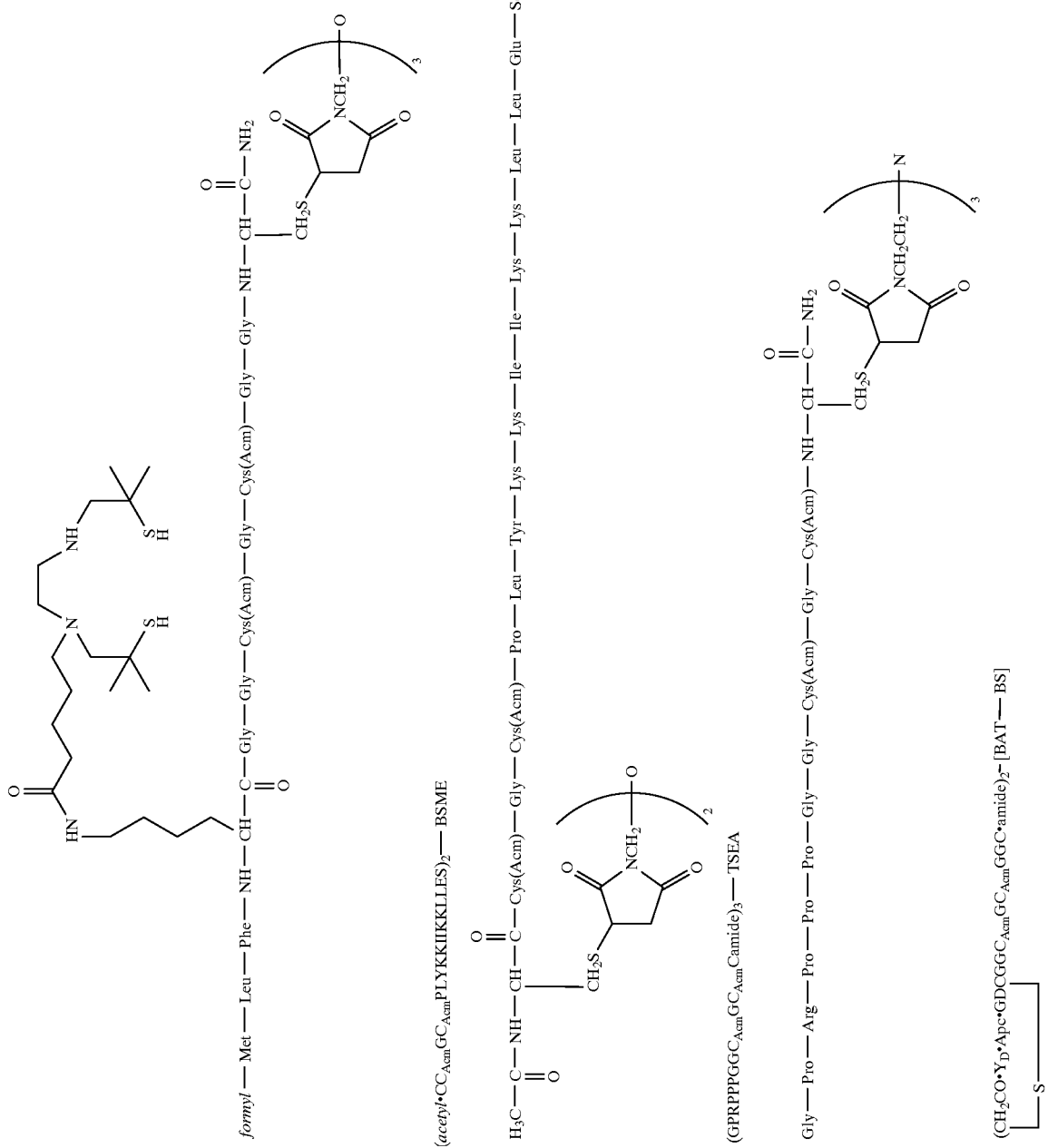

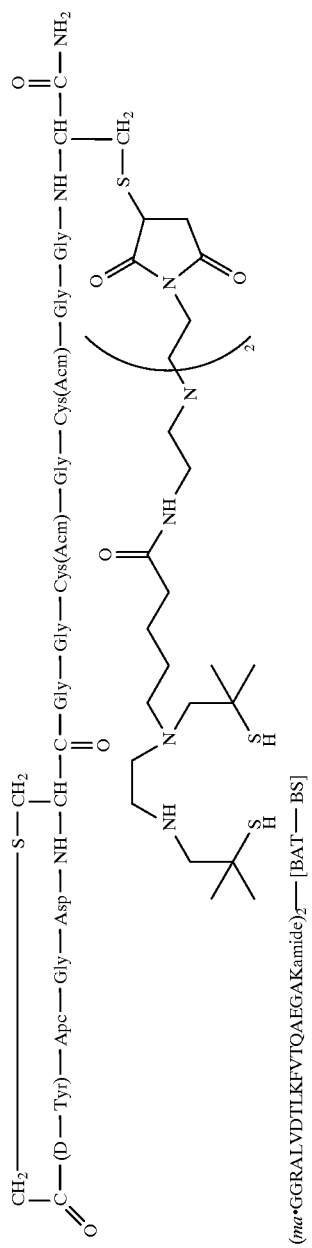
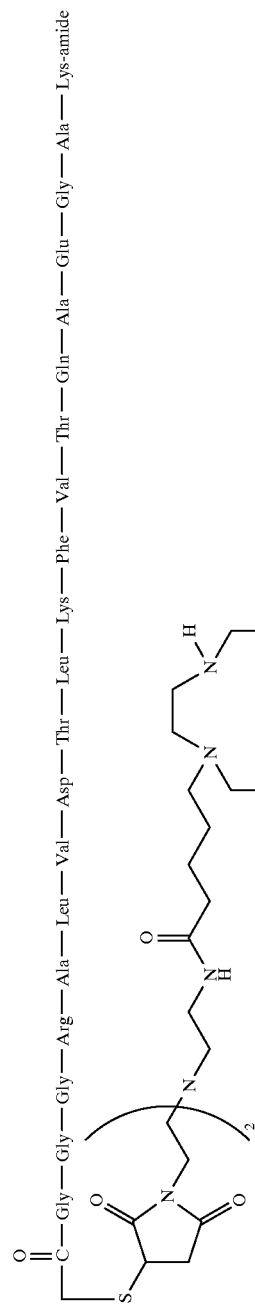
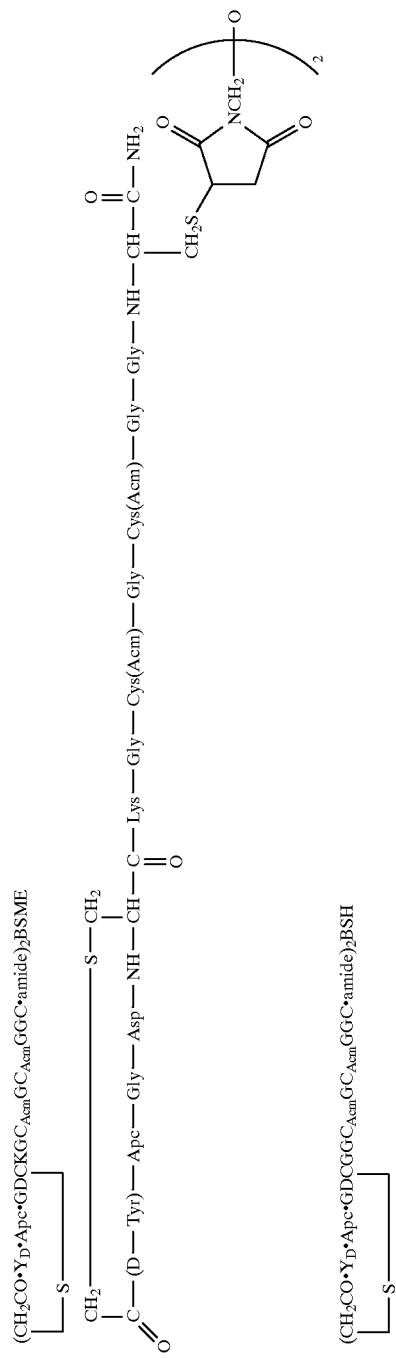

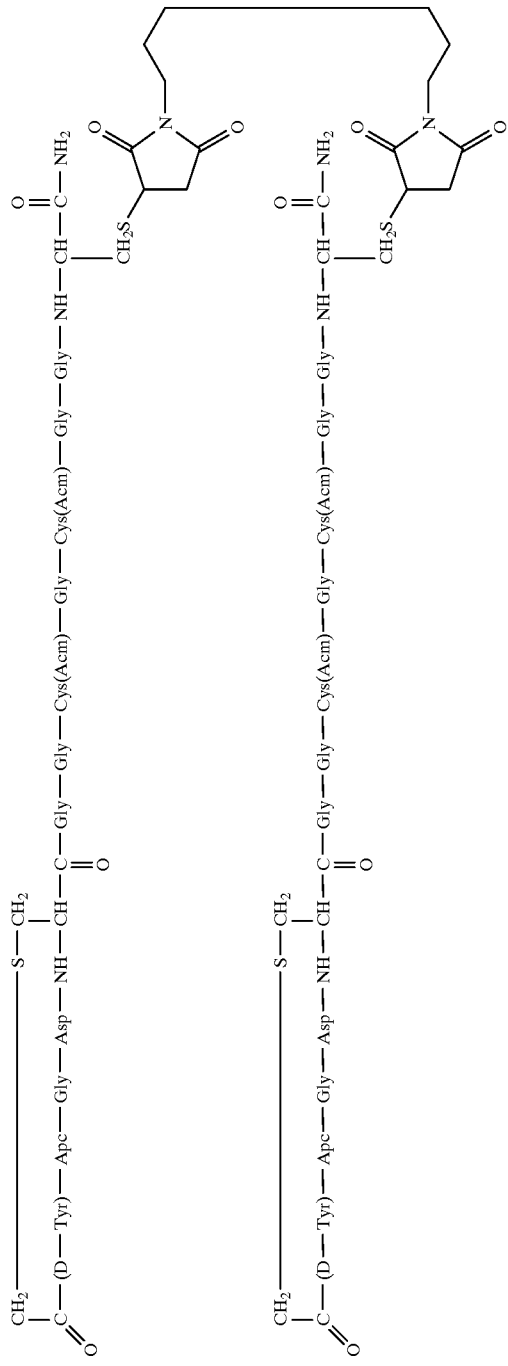
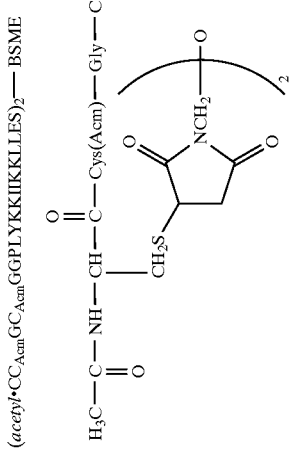
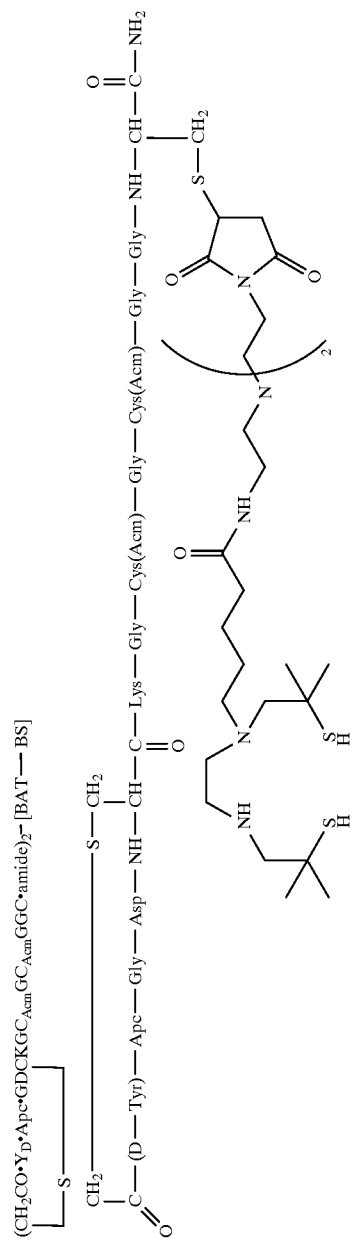

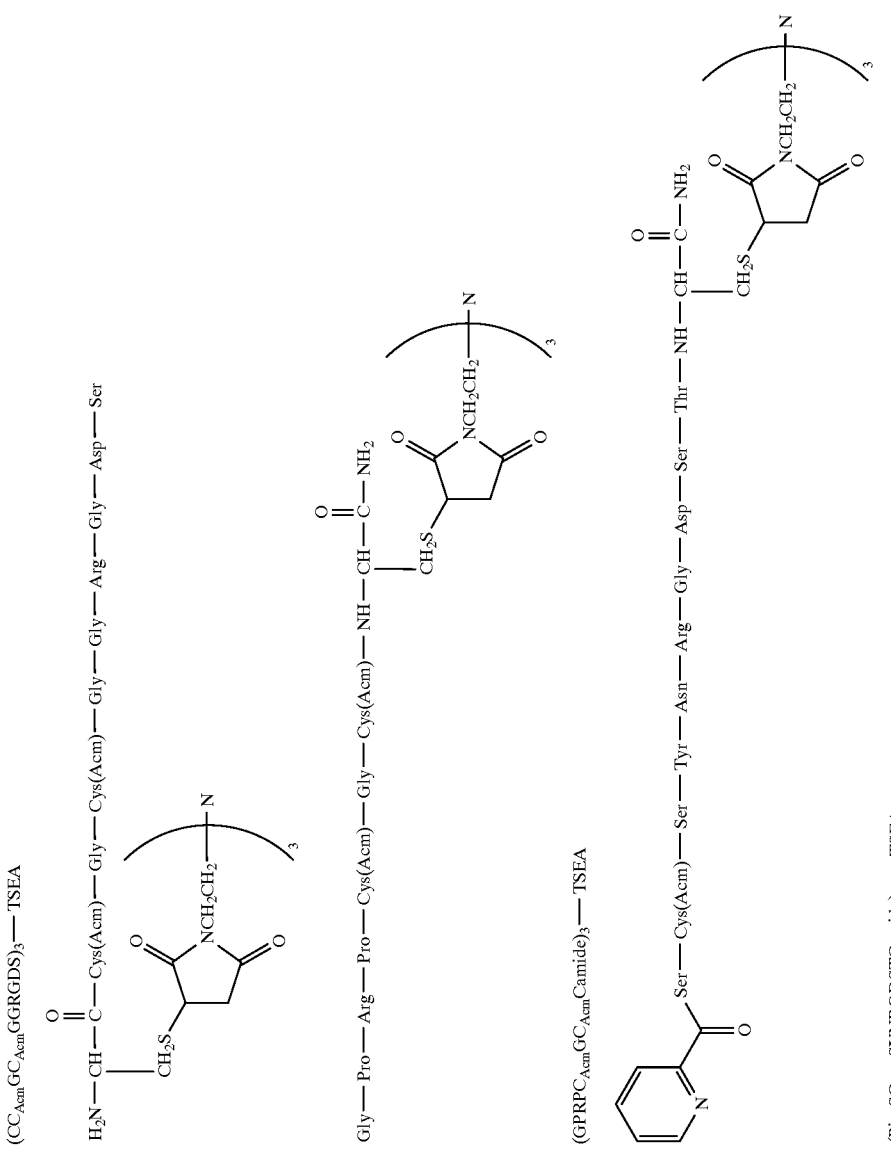

EXAMPLE 5

In Vivo Imaging of Deep Vein Thrombosis using a Tc-99m Labeled Peptide in a Canine Model Mongrel dogs (25–35 lb., fasted overnight) were sedated with a combination of ketamine and aceprozamine intramuscularly and then anesthetized with sodium pentabarbital intravenously. In each animal, an 18gauge angiocath was inserted in the distal half of the right femoral vein and an 8mm Dacron®-entwined stainless steel embolization coil (Cook Co., Bloomington Ind.) was placed in the femoral vein at approximately mid-femur. The catheter was removed, the wound sutured and the placement of the coil documented by X-ray. The animals were then allowed to recover overnight.

One day following coil placement, each animal was re-anesthetized, intravenous saline drips placed in each foreleg and a urinary bladder catheter inserted to collect urine. The animal was placed supine under a gamma camera which was equipped with a low-energy, all purpose collimator and photopeaked for Tc-99m.

Tc-99m labeled peptide [185–370 mBq (5–10 mCi) Tc-99m] was injected sequentially into one foreleg intravenous line at its point of insertion. The second line was maintained for blood collection.

Gamma camera imaging was started simultaneously with injection. Anterior images over the heart were acquired as a dynamic study (10 sec image acquisitions) over the first 10 min, and then as static images at 1, 2, 3 and 4h post-injection. Anterior images over the legs were acquired for 500,000 counts or 20 min (whichever was shorter), at approximately 10–20 min, and at approximately 1, 2, 3 and 4h post-injection. Leg images were collected with a lead shield placed over the bladder.

Following the final image, each animal was deeply anesthetized with pentobarbital. Two blood samples were collected on a cardiac puncture using a heparinized syringe followed by a euthanasing dose of saturated potassium chloride solution administered by intercardiac or bolus intravenous injection. The femoral vein containing the thrombus, a similar section of vein of the contralateral (control) leg, sections of the vessel proximal to the thrombus and samples of thigh muscle were then carefully dissected out. The thrombus, coil and coil Dacron fibres were then dissected free of the vessel. The thrombus, saline-washed vessel samples, coil and coil Dacron fibres were separated, and each sample was placed in a pre-weighed test tube. The samples were weighed and counted in a gamma well counter in the Tc-99m channel, along with known fractions of the injected doses.

Fresh thrombus weight, percent injected dose (% ID)/g in the thrombus and blood obtained just prior to euthanasia and thrombus/blood and thrombus/muscle ratios were determined. From the computer-stored images, thrombus/background ratios were determined by analysis of the counts/pixel measured in regions-of-interest (ROI) drawn over the thrombus and adjacent muscle. Tissue data from these experiments are shown in the following Table. Scintigraphic images showing the location of venous thrombi in vivo detected using Tc-99m labeled peptide P357 are shown in FIG. 1, wherein each of the images represents a scintiphoto taken at the following times post-injection: A=23 min; B=1 h 11 min; C=2 h 19 min; D=3 h 28 min and E=3 h 42 min.

These results demonstrate that deep vein thrombi can be rapidly and efficiently located in vivo using Tc-99m labeled reagents of the invention. Localization was clearly established within 1 h post-injection and persisted, with increasing contrast and focal definition, over nearly 4 h post-injection.

It should be understood that the foregoing disclosure emphasizes certain specific embodiments of the invention and that all modifications or alternatives equivalent thereto are within the spirit and scope of the invention as set forth in the appended claims.

TABLE II

| Peptide | Thrombus/ Background | % ID/g Thrombus | % ID/g Blood | Thrombus/ Blood | Thrombus/ Muscle |
|---|---|---|---|---|---|
| P317 (n = 4) | 2.5[a] | 0.0035 | 0.0011 | 3.8 ± 2.2 | 16 ± 10 |
| P280 (n = 6) | 2.3 ± 0.4 | 0.0059 | 0.0012 | 4.4 ± 1.8 | 11 ± 7 |
| P357 (n = 9) | 2.7 ± 1.0 | 0.019 | 0.0028 | 11 ± 7 | 21 ± 14 |

Values shown are the average ± the standard deviation from the mean;
[n = number of experiments performed with this peptide]
[[a] = n = 2 for this value]

$(CH_2CO.Y_D.Apc.GDCKGC_{Acm}GC_{Acm}GGCamide)_2$-[BAT—BS] = P357

What is claimed is:

1. A reagent for preparing a scintigraphic imaging agent comprising:
    a) at least two specific binding peptides, each peptide being covalently linked to a technetium-99m binding moiety; and
    b) a polyvalent linker covalently linked to each peptide.

2. A reagent for preparing a scintigraphic imaging agent comprising:
    a) at least two specific binding peptides, each peptide being covalently linked to a technetium-99m binding moiety; and
    b) a polyvalent linker covalently linked to each moiety.

3. A reagent for preparing a scintigraphic imaging agent comprising:
    a) a first specific binding peptide covalently linked to a first technetium-99m binding moiety;
    b) a second specific binding peptide covalently linked to a second technetium-99m binding moiety; and
    c) a polyvalent linker covalently linked to the first peptide and to the second technetium-99m binding moiety.

4. A reagent for preparing a scintigraphic imaging agent comprising:
    a) a first specific binding peptide covalently linked to a first polyvalent linker;
    b) a second specific binding peptide covalently linked to a second polyvalent linker; and
    c) a technetium-99m binding moiety linking the first linker and the second peptide.

5. A reagent for preparing a scintigraphic imaging agent comprising:
    a) at least two specific binding peptides, each peptide being covalently linked to a technetium-99m binding moiety;
    b) a first polyvalent linker covalently linked to each peptide; and
    c) a second polyvalent linker covalently linked to the first polyvalent linker.

6. A reagent for preparing a scintigraphic imaging agent comprising:

a) at least two specific binding peptides, each peptide being covalently linked to a technetium-99m binding moiety;

b) a first polyvalent linker covalently linked to each moiety; and c) a second polyvalent linker covalently linked to the first polyvalent linker.

7. A reagent for preparing a scintigraphic imaging agent comprising:

a) at least two specific binding peptides;

b) at least two first polyvalent linkers, wherein each peptide is covalently linked to a first polyvalent linker;

c) a second polyvalent linker covalently linked to each first polyvalent linker; and d) a technetium-99m binding moiety covalently linked to the second polyvalent linker.

8. A reagent for preparing a scintigraphic imaging agent comprising:

a) at least two specific binding peptides;

b) at least two first polyvalent linkers, wherein each peptide is covalently linked to a first polyvalent linker;

c) at least two technetium-99m binding moieties, each covalently linked to a first polyvalent linker; and d) a second polyvalent linker covalently linked to each first polyvalent linker.

9. The reagent of claims 1, 2, 3, 4, 5, 6, 7, or 8, wherein the moiety is selected from the group consisting of:

I

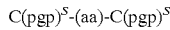

wherein $C(pgp)^S$ is a cysteine having a protected thiol group and (aa) is an amino acid;

II a technetium-99m binding moiety comprising a single thiol group having a formula:

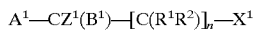

wherein $A^1$ is H, HOOC, H$_2$NOC, or —NHOC;

$B^1$ is SH or NHR$^3$;

$X^1$ is H, methyl, SH or NHR$^3$;

$Z^1$ is H or methyl;

$R^1$ and $R^2$ are independently H or lower alkyl;

$R^3$ is H, lower alkyl or —C=O;

n is 0, 1 or 2;

and where $B^1$ is NHR$^3$, $X^1$ is SH, $Z^1$ is H and n is 1 or 2;

where $X^1$ is NHR$^3$, $B^1$ is SH, $Z^1$ is H and n is 1 or 2;

where $B^1$ is H, $A^1$ is HOOC, H$_2$NOC, or —NHOC, $X^1$ is SH, $Z^1$ is H and n is 0 or 1;

where $Z^1$ is methyl, $X^1$ is methyl, $A^1$ is HOOC, H$_2$NOC, or —NHOC, $B^1$ is SH and n is 0;

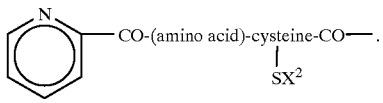

wherein
$X^2$=H or a protecting group;
(amino acid)=any amino acid;

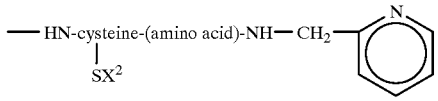

wherein
$X^2$=H or a protecting group;
(amino acid)=any amino acid;

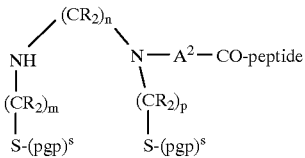

wherein
each R is independently H, CH$_3$ or C$_2$H$_5$;
each (pgp)$^s$ is independently a thiol protecting group or H;
m, n and p are independently 2 or 3;
$A^2$=linear or cyclic lower alkyl, aryl, heterocyclyl, a combination thereof or a substituted derivative thereof; and

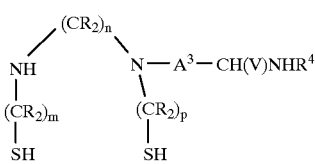

wherein
each R is independently H, CH$_3$ or C$_2$H$_5$;
m, n and p are independently 2 or 3;
$A^3$=linear or cyclic lower alkyl, aryl, heterocyclyl, a combination thereof or a substituted derivative thereof;
V=H or -CO-peptide;
$R^4$=H or peptide;
and wherein when V=H, $R^4$=peptide and when $R^4$=H, V=-CO-peptide.

10. The reagent of claims 1, 2, 3, 4, 5, 6, 7, or 8, wherein each linker comprises at least two functional groups selected from the group consisting of: primary amines, secondary amines, hydroxyl groups, carboxylic acid groups, and thiol-reactive groups.

11. The reagent of claim 10, wherein the functional groups are thiol-reactive groups selected from the groups consisting of maleimido groups, chloroacetyl groups, bromoacetyl groups, and iodoacetyl groups.

12. The reagent of claim 10, wherein the linker is selected from the group consisting of bis-succinimidylmethylether, 4-(2,2-dimethylacetyl)benzoic acid, N-[2-(N'N'-bis(2-succinimidoethyl)aminoethyl)]-$N^6,N^9$-bis(2-methyl-2-mercaptopropyl)-6,9-diazanonanamide, 4-(2,2-dimethylacetyl)benzoic acid, tris(succinimidylethyl)amine, bis-succinimidohexane, 4-(O-CH$_2$CO-Gly-Gly-Cys.amide)acetophenone, a derivative of bis-succinimidylmethylether, a derivative of 4-(2,2-dimethylacetyl)benzoic acid, a derivative of N-[2-(N',N'-bis(2-succinimidoethyl)aminoethyl)]-$N^6,N^9$-bis(2-methyl-2-mercaptopropyl)-6,9-diazanonanamide, a derivative of 4-(2,2-dimethylacetyl)benzoic acid, a derivative of tris(succinimidylethyl)amine, a derivative of bis-succinimidohexane, and a derivative of 4-(O-CH$_2$CO-Gly-Gly-Cys.amide)acetophenone.

13. The reagent of claims 1, 2, 3, 4, 5, 6, 7, or 8, further comprising technetium-99m.

14. A complex formed by reacting the reagent of claims 1, 2, 3, 4, 5, 6, 7, or 8 with technetium-99m and a reducing agent.

15. The complex of claim 14, wherein the reducing agent is selected from the group consisting of a dithionite ion, a stannous ion, and a ferrous ion.

16. A complex formed by reacting the reagent of claims 1, 2, 3, 4, 5, 6, 7, or 8 with technetium-99m by ligand exchange of a prereduced technetium-99m complex.

17. A kit for preparing a radiopharmaceutical preparation, said kit comprising a sealed vial containing a predetermined quantity of the reagent of claims 1, 2, 3, 4, 5, 6, 7, or 8 and a sufficient amount of reducing agent to label the reagent with technetium-99m.

18. A method of labeling a reagent according to claims 1, 2, 3, 4, 5, 6, 7, or 8, comprising the step of reacting the reagent with technetium-99m in the presence of a reducing agent.

19. The method of claim 18, wherein the reducing agent is selected from the group consisting of a dithionite ion, a stannous ion and a ferrous ion.

20. A method of imaging a site within a mammalian body comprising the steps of administering an effective diagnostic amount of the reagent of claim 13 and detecting a radioactive signal from the technetium-99m localized at the site.

21. The method of claim 20, wherein the site is a thrombus.

22. The method of claim 20, wherein the site is an infection.

23. The reagent of claims 1, 2, 3, 4, 5, 6, 7, or 8, wherein the peptide is chemically synthesized in vitro.

24. The reagent of claim 23, wherein the peptide is synthesized by solid phase peptide synthesis.

25. The reagent of claims 1, 2, 3, 4, 5, 6, 7, or 8, wherein the moiety is covalently linked to the peptide during in vitro chemical synthesis.

26. The reagent of claim 25, wherein the moiety is covalently linked to the peptide during solid phase peptide synthesis.

27. A composition comprising a reagent selected from the group consisting of:

(acetyl.F$_{D\_k\ PRPG)2}$KGGGCamide;

(acetyl.CC$_{Acm}$GC$_{Acm}$PLYKKIIKKLLES)$_2$-BSME;

(acetyl.CC$_{Acm}$GC$_{Acm}$GGPLYKKIIKKLLES )$_2$-BSME;

(formyl.MLF(N$_\epsilon$-BAT)GGC$_{Acm}$GC$_{Acm}$GGC.amide)$_2$-BSME;

(GPRPPPGGC$_{Acm}$GC$_{Acm}$GGCamide)$_3$-TSEA;

(Pic.SC$_{Acm}$SYNRGDSTCamide)$_3$-TSEA;

(ma.GGGRALVDTLKFVTQAEGAKamide)$_2$-(BAT-BS); and (Pic.GC$_{Acm}$RALVDTLKFVTQAEGAKCamide)$_3$-TSEA.

28. The composition of claim 27, further comprising technetium-99m.

29. A kit for preparing a radiopharmaceutical preparation, said kit comprising a sealed vial the composition of claim 27 and a sufficient amount of a reducing agent to label the reagent with technetium-99m.

30. A reagent having a formula:

* * * * *